(12) United States Patent
Kanzaki et al.

(10) Patent No.: US 10,307,506 B2
(45) Date of Patent: Jun. 4, 2019

(54) PROCESS FOR PRODUCING WATER-ABSORBING RESIN

(75) Inventors: Syuji Kanzaki, Hyogo (JP); Sumio Okuda, Hyogo (JP); Kunihiko Ishizaki, Hyogo (JP); Satoshi Matsumoto, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 13/634,128

(22) PCT Filed: Mar. 14, 2011

(86) PCT No.: PCT/JP2011/055979
§ 371 (c)(1),
(2), (4) Date: Sep. 11, 2012

(87) PCT Pub. No.: WO2011/111857
PCT Pub. Date: Sep. 15, 2011

(65) Prior Publication Data
US 2013/0005919 A1    Jan. 3, 2013

(30) Foreign Application Priority Data

Mar. 12, 2010 (JP) ................. 2010-055236
Mar. 12, 2010 (JP) ................. 2010-055237
Mar. 12, 2010 (JP) ................. 2010-055238

(51) Int. Cl.
*C08F 6/00* (2006.01)
*C08J 3/12* (2006.01)
(Continued)

(52) U.S. Cl.
CPC ............. *A61L 15/56* (2013.01); *A61L 15/60* (2013.01); *B01J 20/261* (2013.01); *B01J 20/267* (2013.01);
(Continued)

(58) Field of Classification Search
CPC ...... A61L 15/56; A61L 15/60; C08J 2300/14; C08J 3/12; B01J 20/261; B01J 2220/68; C08F 6/008
(Continued)

(56) References Cited

U.S. PATENT DOCUMENTS

| 4,734,478 A | 3/1988 | Tsubakimoto et al. |
| 4,755,562 A | 7/1988 | Alexander et al. |

(Continued)

FOREIGN PATENT DOCUMENTS

| EP | 0349240 | 1/1990 |
| EP | 0450923 | 10/1991 |

(Continued)

OTHER PUBLICATIONS

2009 American Control Conference, Hyatt Regency Riverfront, St. Louis MO; Jun. 2009.*

(Continued)

*Primary Examiner* — Liam J Heincer
(74) *Attorney, Agent, or Firm* — Dickinson Wright PLLC (57) ABSTRACT

The disclosed process for continuously producing a water-absorbing resin comprising a plurality of joined continuous steps; a polymerization step of polymerizing an aqueous unsaturated monomer solution, a drying step of drying a particulated water-containing gel-like crosslinked polymer obtained in a finely crushing step during the polymerization or after the polymerization, a pulverizing step after the drying, a classification step after the drying, and a surface treatment step for the water-absorbing resin powder after the classification step. In the process, with some of the above steps kept running, the other steps are interrupted, and subsequently all the steps are restarted.

16 Claims, 1 Drawing Sheet

(51) Int. Cl.
  *C08J 3/24* (2006.01)
  *A61L 15/56* (2006.01)
  *A61L 15/60* (2006.01)
  *B01J 20/26* (2006.01)
(52) U.S. Cl.
  CPC .............. *C08F 6/008* (2013.01); *C08J 3/12* (2013.01); *C08J 3/122* (2013.01); *C08J 3/245* (2013.01); *B01J 2220/68* (2013.01); *C08J 2300/14* (2013.01); *C08J 2333/02* (2013.01)
(58) Field of Classification Search
  USPC .................... 525/384; 526/317.1, 318.2, 223
  See application file for complete search history.

(56) References Cited

U.S. PATENT DOCUMENTS

| | | | |
|---|---|---|---|
| 4,783,510 A | 11/1988 | Saotome | |
| 4,824,901 A | 4/1989 | Alexander et al. | |
| 4,893,999 A | 1/1990 | Chmelir et al. | |
| 4,920,202 A | 4/1990 | Irie et al. | |
| 5,005,771 A | 4/1991 | Reh et al. | |
| 5,140,076 A | 8/1992 | Hatsuda et al. | |
| 5,206,205 A | 4/1993 | Tsai | |
| 5,229,487 A | 7/1993 | Tsubakimoto et al. | |
| 5,385,983 A | 1/1995 | Graham | |
| 5,409,771 A | 4/1995 | Dahmen et al. | |
| 5,422,405 A | 6/1995 | Dairoku et al. | |
| 5,462,972 A | 10/1995 | Smith et al. | |
| 5,597,873 A | 1/1997 | Chambers et al. | |
| 5,610,208 A | 3/1997 | Dairoku et al. | |
| 5,610,220 A | 3/1997 | Klimmek et al. | |
| 5,633,316 A | 5/1997 | Gartner et al. | |
| 5,669,894 A | 9/1997 | Goldman et al. | |
| 5,672,633 A | 9/1997 | Brehm et al. | |
| 5,674,633 A | 10/1997 | Saunders et al. | |
| 5,945,495 A | 8/1999 | Daniel et al. | |
| 5,981,070 A | 11/1999 | Ishizaki et al. | |
| 6,071,976 A | 6/2000 | Dairoku et al. | |
| 6,164,455 A | 12/2000 | Kakita et al. | |
| 6,187,902 B1 | 2/2001 | Yanase et al. | |
| 6,207,796 B1 | 3/2001 | Dairoku et al. | |
| 6,228,930 B1 | 5/2001 | Dairoku et al. | |
| 6,239,230 B1 | 5/2001 | Eckert et al. | |
| 6,241,928 B1 | 6/2001 | Hatsuda et al. | |
| 6,254,990 B1 | 7/2001 | Ishizaki et al. | |
| 6,265,488 B1 | 7/2001 | Fujino et al. | |
| 6,291,635 B1 | 9/2001 | Maeda et al. | |
| 6,297,139 B1 | 10/2001 | Lin | |
| 6,300,423 B1 | 10/2001 | Engelhardt et al. | |
| 6,372,852 B2 | 4/2002 | Hitomi et al. | |
| 6,388,000 B1 | 5/2002 | Irie et al. | |
| 6,458,921 B1 | 10/2002 | Dairoku et al. | |
| 6,472,478 B1 | 10/2002 | Funk et al. | |
| 6,503,979 B1 | 1/2003 | Funk et al. | |
| 6,514,615 B1 | 2/2003 | Sun et al. | |
| 6,559,239 B1 | 5/2003 | Riegel et al. | |
| 6,605,673 B1 | 8/2003 | Mertens et al. | |
| 6,620,889 B1 | 9/2003 | Mertens et al. | |
| 6,620,899 B1 | 9/2003 | Morken et al. | |
| 6,641,064 B1 | 11/2003 | Dentler et al. | |
| 6,657,015 B1 | 12/2003 | Riegel et al. | |
| 6,710,141 B1 | 3/2004 | Heide et al. | |
| 6,716,894 B2 | 4/2004 | Kajikawa et al. | |
| 6,720,389 B2 | 4/2004 | Hatsuda et al. | |
| 6,727,345 B2 | 4/2004 | Kajikawa et al. | |
| 6,809,158 B2 | 10/2004 | Ikeuchi et al. | |
| 6,817,557 B2 | 11/2004 | Kakita et al. | |
| 6,906,159 B2 | 6/2005 | Dairoku et al. | |
| 6,987,151 B2 | 1/2006 | Gartner et al. | |
| 7,091,253 B2 | 8/2006 | Dairoku et al. | |
| 7,098,284 B2 | 8/2006 | Torii et al. | |
| 7,157,141 B2 | 1/2007 | Inger et al. | |
| 7,183,456 B2 | 2/2007 | Hatsuda et al. | |
| 7,193,006 B2 | 3/2007 | Ishizaki et al. | |
| 7,312,278 B2 | 12/2007 | Nakashima et al. | |
| 7,378,453 B2 | 5/2008 | Nogi et al. | |
| 7,473,739 B2 | 1/2009 | Dairoku et al. | |
| 7,682,702 B2 | 3/2010 | Nitschke | |
| 7,960,490 B2 | 6/2011 | Funk et al. | |
| 7,967,148 B2 | 6/2011 | Stueven et al. | |
| 8,071,202 B2 | 12/2011 | Furno et al. | |
| 8,104,621 B2 | 1/2012 | Weismantel et al. | |
| 8,138,292 B2 | 3/2012 | Matsumoto et al. | |
| 8,148,485 B2* | 4/2012 | Nogi et al. | 526/317.1 |
| 8,188,163 B2 | 5/2012 | Matsumoto et al. | |
| 2003/0020199 A1 | 1/2003 | Kajikawa et al. | |
| 2003/0087983 A1 | 5/2003 | Kajikawa et al. | |
| 2004/0110006 A1 | 6/2004 | Ishizaki et al. | |
| 2004/0240316 A1 | 12/2004 | Nogi et al. | |
| 2005/0029352 A1 | 2/2005 | Spears | |
| 2005/0048221 A1 | 3/2005 | Irie et al. | |
| 2005/0070671 A1 | 3/2005 | Torii et al. | |
| 2005/0215734 A1 | 9/2005 | Dairoku et al. | |
| 2005/0288182 A1 | 12/2005 | Torii et al. | |
| 2006/0057389 A1 | 3/2006 | Reimann et al. | |
| 2006/0073969 A1 | 4/2006 | Torii et al. | |
| 2006/0204755 A1 | 9/2006 | Torii et al. | |
| 2006/0247351 A1 | 11/2006 | Torii et al. | |
| 2007/0041796 A1 | 2/2007 | Irie et al. | |
| 2007/0078231 A1 | 4/2007 | Shibata et al. | |
| 2007/0106013 A1 | 5/2007 | Adachi et al. | |
| 2007/0123624 A1 | 5/2007 | Otten et al. | |
| 2007/0141338 A1 | 6/2007 | Ishizaki et al. | |
| 2007/0149691 A1 | 6/2007 | Ishizaki et al. | |
| 2007/0149760 A1 | 6/2007 | Kadonaga et al. | |
| 2007/0161759 A1 | 7/2007 | Riegel et al. | |
| 2007/0173610 A1 | 7/2007 | Wada et al. | |
| 2007/0293632 A1 | 12/2007 | Riegel et al. | |
| 2008/0004408 A1 | 1/2008 | Stueven et al. | |
| 2008/0021150 A1 | 1/2008 | Becker et al. | |
| 2008/0202987 A1 | 8/2008 | Weismantel et al. | |
| 2008/0214749 A1 | 9/2008 | Weismantel et al. | |
| 2008/0221277 A1 | 9/2008 | Walden et al. | |
| 2008/0280128 A1 | 11/2008 | Furno et al. | |
| 2008/0287631 A1 | 11/2008 | Nitschke | |
| 2009/0022603 A1 | 1/2009 | Feise et al. | |
| 2009/0060660 A1 | 3/2009 | Funk et al. | |
| 2009/0105389 A1 | 4/2009 | Walden et al. | |
| 2009/0194462 A1 | 8/2009 | Stueven et al. | |
| 2009/0202805 A1 | 8/2009 | Furno et al. | |
| 2009/0227741 A1 | 9/2009 | Walden et al. | |
| 2009/0266747 A1 | 10/2009 | Stueven et al. | |
| 2009/0275470 A1 | 11/2009 | Nagasawa et al. | |
| 2009/0314258 A1 | 12/2009 | Azou | |
| 2009/0321682 A1 | 12/2009 | Kajikawa et al. | |
| 2010/0001233 A1 | 1/2010 | Funk et al. | |
| 2010/0016522 A1 | 1/2010 | Stueven et al. | |
| 2010/0140546 A1 | 6/2010 | Barthel et al. | |
| 2010/0249320 A1 | 9/2010 | Matsumoto et al. | |
| 2011/0003926 A1 | 1/2011 | Nogi et al. | |
| 2011/0006140 A1 | 1/2011 | Ishizaki et al. | |
| 2011/0009590 A1 | 1/2011 | Matsumoto et al. | |
| 2011/0011491 A1 | 1/2011 | Matsumoto et al. | |
| 2011/0015351 A1 | 1/2011 | Nogi et al. | |
| 2011/0021725 A1 | 1/2011 | Takaai et al. | |
| 2011/0028670 A1 | 2/2011 | Matsumoto et al. | |
| 2011/0039961 A1 | 2/2011 | Matsumoto et al. | |
| 2011/0059329 A1 | 3/2011 | Dobrawa et al. | |
| 2011/0088806 A1 | 4/2011 | Nogi et al. | |
| 2011/0110730 A1 | 5/2011 | Nogi et al. | |
| 2011/0166300 A1 | 7/2011 | Dairoku et al. | |
| 2012/0157625 A1 | 6/2012 | Kitano et al. | |
| 2012/0157635 A1 | 6/2012 | Nogi et al. | |
| 2012/0157650 A1 | 6/2012 | Nogi et al. | |
| 2012/0172536 A1 | 7/2012 | Nogi et al. | |
| 2012/0220733 A1 | 8/2012 | Machida et al. | |
| 2012/0220745 A1 | 8/2012 | Machida et al. | |

(56) References Cited

U.S. PATENT DOCUMENTS

| | | |
|---|---|---|
| 2013/0281594 A1 | 10/2013 | Dobrawa et al. |
| 2014/0058346 A1 | 2/2014 | Wada et al. |

FOREIGN PATENT DOCUMENTS

| | | |
|---|---|---|
| EP | 0450924 | 10/1991 |
| EP | 0534228 | 3/1993 |
| EP | 0603292 | 6/1994 |
| EP | 0605150 | 7/1994 |
| EP | 0668080 | 8/1995 |
| EP | 0812873 | 12/1997 |
| EP | 1422257 | 5/2004 |
| EP | 1426402 | 6/2004 |
| EP | 1824910 | 8/2007 |
| EP | 1848758 | 10/2007 |
| EP | 1949011 | 7/2008 |
| EP | 2057228 | 5/2009 |
| EP | 2189478 | 5/2010 |
| EP | 2253375 | 11/2010 |
| EP | 2258749 | 12/2010 |
| EP | 2261148 | 12/2010 |
| EP | 2471843 | 7/2012 |
| EP | 2479195 | 7/2012 |
| JP | 54-053165 | 4/1979 |
| JP | 64-060683 | 3/1989 |
| JP | 1060683 | 3/1989 |
| JP | 7-224304 | 8/1995 |
| JP | 7-242709 | 9/1995 |
| JP | 7-270070 | 10/1995 |
| JP | 8-073518 | 3/1996 |
| JP | 10-059534 | 3/1998 |
| JP | 2000-063527 | 2/2000 |
| JP | 2000-143720 | 5/2000 |
| JP | 2001-018222 | 1/2001 |
| JP | 2002-226599 | 8/2002 |
| JP | 2003-012812 | 1/2003 |
| JP | 2003-082107 | 3/2003 |
| JP | 2004-197087 | 7/2004 |
| JP | 2004-345804 | 12/2004 |
| JP | 2004-352941 | 12/2004 |
| JP | 2006-160774 | 6/2006 |
| JP | 2006-198529 | 8/2006 |
| JP | 2007-224224 | 9/2007 |
| JP | WO2009/113672 * | 9/2009 |
| JP | 2009-256687 | 11/2009 |
| JP | 2009-545635 | 12/2009 |
| JP | 2010-053296 | 3/2010 |
| WO | 99/42494 | 8/1999 |
| WO | 99/42496 | 8/1999 |
| WO | 99/43720 | 9/1999 |
| WO | 2004/069293 | 8/2004 |
| WO | 2004/069915 | 8/2004 |
| WO | 2009/123193 | 8/2004 |
| WO | 2005/016393 | 2/2005 |
| WO | 2005/056177 | 6/2005 |
| WO | 2006/034806 | 4/2006 |
| WO | 2006/074816 | 7/2006 |
| WO | 2006/082188 | 8/2006 |
| WO | 2006/082189 | 8/2006 |
| WO | 2006/082197 | 8/2006 |
| WO | 2006/111402 | 10/2006 |
| WO | 2006/111403 | 10/2006 |
| WO | 2006/111404 | 10/2006 |
| WO | 2007/065840 | 6/2007 |
| WO | 2007/104673 | 9/2007 |
| WO | 2007/104676 | 9/2007 |
| WO | 2007/121037 | 10/2007 |
| WO | 2008/003672 | 1/2008 |
| WO | 2008/009642 | 1/2008 |
| WO | 2008/009842 | 1/2008 |
| WO | 2008/009843 | 1/2008 |
| WO | 2008/015946 | 2/2008 |
| WO | 20081034786 | 3/2008 |
| WO | 2008/003675 | 4/2008 |
| WO | 2008/037673 | 4/2008 |
| WO | 2008/037675 | 4/2008 |
| WO | 2008/037676 | 4/2008 |
| WO | 2008/087114 | 7/2008 |
| WO | 2008/123477 | 10/2008 |
| WO | 2009/005114 | 1/2009 |
| WO | 2009/028568 | 3/2009 |
| WO | 2009/113671 | 9/2009 |
| WO | 2009/113672 | 9/2009 |
| WO | 2009/113678 | 9/2009 |
| WO | 2009/113679 | 9/2009 |
| WO | 2009/119754 | 9/2009 |
| WO | 2009/119756 | 10/2009 |
| WO | 2009/123197 | 10/2009 |
| WO | 2010/032694 | 3/2010 |
| WO | 2011/026876 | 3/2011 |

OTHER PUBLICATIONS

International Search Report for PCT/JP2011/055979, dated Apr. 5, 2011.
Office Action dated Dec. 5, 2012 in U.S. Appl. No. 13/578,118.
Office Action dated Jun. 20, 2013 in U.S. Appl. No. 13/578,118.
Notice of Reasons for Rejection dated Feb. 25, 2014 in JP Application No. 2012-504555, and English translation thereof.
Notice of Reasons for Rejection, dated Nov. 26, 2013, for JP 2011-553903, and English translation thereof.
Notice of Reasons for Rejection, dated Nov. 26, 2013, for JP 2012-504554, and English translation thereof.
Notice of Reasons for Rejection, dated Nov. 26, 2013, for JP 2012-504555, and English translation thereof.
Notice of Reasons for Rejection, dated Nov. 26, 2013, for JP 2012-504556, and English translation thereof.
Office Action dated Nov. 21, 2014 issued in related U.S. Appl. No. 13/634,151.
Office Action dated Dec. 23, 2014 issued in related U.S. Appl. No. 13/634,167.
Notice of Reasons for Rejection dated Apr. 1, 2014 in JP Application No. 2012-504556, and English translation thereof.
Notice of Reasons for Rejection dated Apr. 1, 2014 in JP Application No. 2011-553903, and English translation thereof.
Office Action dated Jun. 19, 2014 issued in U.S. Appl. No. 13/578,118.
Office Action dated Jul. 7, 2014 issued in U.S. Appl. No. 13/634,151.
Office Action dated Aug. 12, 2014 issued in related U.S. Appl. No. 13/634,167.
Extended European Search Report, dated Nov. 5, 2014, for EP Application No. 11742329.3.
Extended European Search Report, dated Oct. 21, 2014, for EP Application No. 11753511.2.
Extended European Search Report, dated Oct. 23, 2014, for EP Application No. 11753510.4.
Extended European Search Report, dated Oct. 17, 2014, for EP Application No. 11753512.0.
Communication Pursuant to Rule 114(2) Epc, Observations by a Third Party Concerning the Patentability of the Invention, dated Oct. 8, 2015, 126 pages.
European Office Action dated Nov. 11, 2015 that issued in the counterpart Patent Application No. 11 753 512.0.
Final Office Action dated Mar. 3, 2015 issued in related U.S. Appl. No. 13/578,118.
Office Action dated Apr. 17, 2015 issued in related U.S. Appl. No. 13/634,151.
Advisory Action dated May 1, 2015 issued in related U.S. Appl. No. 13/634,167.
Advisory Action, dated Mar. 4, 2015, issued in related U.S. Appl. No. 13/634,151.
European Office Action dated Sep. 28, 2016 which issued in the corresponding Patent Application No. 11 742 329.3.
U.S. Office Action dated Mar. 22, 2017 which issued in corresponding U.S. Appl. No. 13/578,118.
U.S. Office Action dated May 31, 20916 that issued in a corresponding U.S. Appl. No. 13/578,118.
European Office Action dated May 14, 2018 issued in the corresponding Patent Application No. 11753511.2.

(56) References Cited

OTHER PUBLICATIONS

European Office Action dated May 14, 2018 issued in the corresponding Patent Application No. 11753510.4.

* cited by examiner

PROCESS FOR PRODUCING WATER-ABSORBING RESIN

TECHNICAL FIELD

The present invention relates to a process for producing a water-absorbing resin. More concretely, the present invention relates to a method for providing a water-absorbing resin with high physical properties by uniform drying after polymerization and surface cross-linking in a process for continuously producing a water-absorbing resin in a huge scale involving joined continuous steps.

BACKGROUND ART

A water-absorbing resin (SAP/Super Absorbent Polymer) is a water-swelling and water-insoluble polymer gelling agent and has been used for mainly disposable uses including absorbing articles such as paper diapers and sanitary napkins, as well as water retention agents for agriculture and horticulture, water-stopping materials for industrial use, and the like. A large number of monomers and hydrophilic polymers have been proposed as raw materials for such a water-absorbing resin and particularly, poly(acrylic acid (salt))-type water-absorbing resins using acrylic acid and/or a salt thereof as a monomer have been industrially used most frequently owing to their high water absorbent capability.

Such a water-absorbing resin can be obtained by finely crushing a water-containing gel-like polymer, which is obtained by polymerizing an aqueous monomer solution, during or after the polymerization, and drying the obtained particulated water-containing gel-like crosslinked polymer. After drying, if necessary, a pulverizing step and a classification step are carried out and arbitrarily, the obtained product is subjected to surface-crosslinking before drying or after drying. One or more steps such as a fine powder recovery step, an undried matter removal step after drying, a packaging step, and an addition step of adding other additives (fine particles, a deodorant, an antibacterial agent, and the like) may also be carried out arbitrarily. A method to be employed as a common polymerization method is aqueous solution polymerization or reverse-phase suspension polymerization and the product form is generally a powder of about 10 to 1000 μm. Such a process for producing a water-absorbing resin involving many steps is exemplified in Patent Documents 1 to 13 or the like.

PRIOR ART DOCUMENTS

Patent Documents

Patent Document 1: WO No. 2009/113679 pamphlet
Patent Document 2: WO No. 2009/113678 pamphlet
Patent Document 3: WO No. 2009/113671 pamphlet
Patent Document 4: WO No. 2009/113672 pamphlet
Patent Document 5: WO No. 2009/119754 pamphlet
Patent Document 6: WO No. 2009/123197 pamphlet
Patent Document 7: U.S. Pat. No. 6,716,894
Patent Document 8: U.S. Pat. No. 6,727,345
Patent Document 9: U.S. Pat. No. 6,164,455
Patent Document 10: U.S. Pat. No. 6,817,557
Patent Document 11: U.S. Pat. No. 6,641,064
Patent Document 12: U.S. Pat. No. 6,291,635
Patent Document 13: EP Patent No. 1949011

SUMMARY OF THE INVENTION

Problems to be Solved by the Invention

In recent years, because of increase of the demand for paper diapers, and the like, production scale of the water-absorbing resin has been becoming wider and it leads to a tendency of scale up for one line of production apparatus and increase of polymerization concentration (increase of concentration of an aqueous monomer solution, e.g., disclosed in Patent Document 7). In order to satisfy various high levels of requests from users, a wide variety of products of water-absorbing resins have been developed. Accordingly, in the present situation, there are many steps and many additives employed after the drying step: for example, a pulverizing step, a classification step, a surface treatment step (particularly, a surface-crosslinking step), a conveying step, a granulation step, an additive addition step, a fine powder recovery step, and the like, according to the above-mentioned patent documents, etc.

Therefore, the present situation is that a lot of models are produced through many steps in a single plant. The respective steps are sometimes carried out in a batch method, but in general, the main stream is a continuous process. The process in which the respective steps are joined is as a whole process a substantially continuous process for production (even if some steps are carried out in a batch method). In addition, substantially continuous means that even in the case of batch steps, the steps are repeatedly continuously carried out. For example, it means a state where the hydrogel or a dried material thereof is subjected to a storage step after repeated batch steps to be continuously supplied to continuous steps (even if some batch steps are involved) and these steps are regarded as continuous as a whole process.

In a process for producing a water-absorbing resin which involves many steps, the continuous flow of a water-absorbing resin or a hydrogel thereof sometimes stops in a production plant because of periodic maintenance or a temporary trouble (an operation trouble in some steps). Patent Documents 9 to 12 disclose such a trouble (stop of operation) in a pulverizing step, a conveying step, or a storage step.

In the case of joined steps, if even a few steps are stopped, the entire plant in which the steps are joined has to be stopped and, therefore, there occurs problems that, at the time of restarting, the quality is not stable, excess energy is required for restarting the operation, an excess load is applied to an apparatus (e.g., it can be confirmed by increase of the power consumption) and the like, and in the worst case, the operation may be stopped. In addition, a colored foreign matter (a discolored material of mainly a water-absorbing resin) may contaminate a water-absorbing resin at the time the operation is restarted.

Solutions to the Problems

To solve the above-mentioned problems, the inventors of the present invention have made earnest investigations and finally have found that the above-mentioned problems can be solved by controlling a method of interrupting a plurality of joined continuous steps.

That is, the present invention provides a process for continuously producing a water-absorbing resin comprising a plurality of joined continuous steps; a polymerization step of polymerizing an aqueous unsaturated monomer solution, a drying step of drying a particulated water-containing gel-like crosslinked polymer obtained in a finely crushing step during the polymerization or after the polymerization, a pulverizing step after the drying, a classification step after the drying, and a surface treatment step for the water-absorbing resin powder after the classification step, wherein with some of the above steps kept running, the other steps are interrupted, and subsequently all the steps are restarted.

Effects of the Invention

In continuous production of a water-absorbing resin, particularly in continuous production for not less than 1 ton per hour, the water-absorbing resin can be stably produced without coloration.

MODE FOR CARRYING OUT THE INVENTION

Hereinafter, a method for producing the water-absorbing resin of the present invention will be described in detail; however, the scope of the present invention is not restricted to the following description, and those other than the following examples can be properly modified and carried out in a range where the gist of the present invention is not impaired. Specifically, the present invention is not limited to each of the following embodiments, and various modifications can be made within a range shown by the claims and embodiments carried out by properly combining each technical means disclosed with different embodiments are also included within the technical scope of the present invention.

[1] Definition of Terms (1-1) Water-Absorbing Resin

In the present invention, the "water-absorbing resin" means a water-swelling and water-insoluble polymer gelling agent. The "water-swelling" means that CRC (absorption capacity without load) defined in ERT 441.2-02 is indispensably 5 [g/g] or more and the "water-insoluble" means that Ext (extractables) defined in ERT 470.2-02 is indispensably 0 to 50 mass %.

The water-absorbing resin can be properly designed in accordance with the use and is not particularly limited, and is preferably a hydrophilic crosslinked polymer obtained by crosslinking polymerization of a carboxyl group-containing unsaturated monomer. The water-absorbing resin is not limited to the case in which the entire amount (100% by mass) is in the form of polymer, and may contain other additives and the like to the extent of retaining the above-mentioned characteristics. That is, even a water-absorbing resin composition is generally named as a water-absorbing resin in the present invention. The content of the polyacrylic acid (salt)-type water-absorbing resin is preferably 70 to 99.9 mass % relative to the entire water-absorbing resin, more preferably 80 to 99.7 mass %, and still more preferably 90 to 99.5 mass %. The components other than the water-absorbing resin are preferably water from the viewpoint of the water absorption speed and impact resistance of powder (particles) and may include, if necessary, additives described below.

(1-2) Polyacrylic Acid (Salt)-Type Water-Absorbing Resin

In the present invention, the "polyacrylic acid (salt)-type water-absorbing resin" means a water-absorbing resin having a unit derived from acrylic acid and/or a salt thereof (hereinafter, referred to as an acrylic acid (salt)) as a main repeating unit. Concretely, it means a polymer inevitably containing an acrylic acid (salt) in an amount of 50 to 100 mol %, preferably 70 to 100 mol %, more preferably 90 to 100 mol %, and particularly preferably substantially 100 mol % in the total monomers (excluding a crosslinking agent) used for polymerization. The salt as the polymer essentially contains a water-soluble salt, and preferably contains a monovalent salt, still more preferably an alkali metal salt or ammonium salt, particularly an alkali metal salt, and further sodium salt.

(1-3) Initial Color Hue and Coloration with Time

In the present invention, the "initial color hue" means the color hue of a water-absorbing resin immediately after production or immediately after shipment to users, and in general, it is controlled based on the color hue before shipment from a plant. A method for measuring the color hue may be methods (Lab value, YI value, WB value, etc.) described in WO No. 2009/005114.

The "coloration with time" means change of color hue of a water-absorbing resin caused during long time storage in an unused sate or caused during distribution. Since a water-absorbing resin is colored with time, the commodity value of paper diapers may be deteriorated. The coloration with time is caused during several months to several years and therefore, it is verified by an accelerating test (accelerating test under high temperature and high humidity) disclosed in WO No. 2009/005114.

(1-4) EDANA and ERT

The "EDANA" is an abbreviation of European Disposables and Nonwovens Associations. "ERT" is an abbreviation of measurement method (EDANA Recommended Test Method) of a water-absorbing resin on the basis of European Standards (almost Global Standards). In this specification, unless otherwise specified, the physical properties of a water-absorbing resin or the like are measured based on ERT original text (Published Literature: revised in 2002).

(a) "CRC" (ERT441.2-02)

The "CRC" is an abbreviation for Centrifuge Retention Capacity and means absorption capacity without load (simply sometimes referred to as "absorption capacity"). Specifically, the CRC is the absorption capacity (unit; g/g) after a water-absorbing resin is freely swollen in 0.9 mass % saline solution for 30 minutes and then dehydrated in a centrifuge.

(b) "AAP" (ERT442.2-02)

The "AAP" is an abbreviation for Absorption Against Pressure and means absorption capacity under load. Specifically, the AAP is the absorption capacity (unit; g/g) in 0.9 mass % saline solution for 1 hour under a load of 2.06 kPa (0.3 psi, 21 [g/cm$^2$]). In the present invention, the AAP was measured under a loading condition of 2.06 kPa (0.3 psi, 21 [g/cm$^2$]) or 4.83 kPa (0.7 psi, 50 [g/cm$^2$]).

(c) "Ext" (ERT470.2-02)

The "Ext" is an abbreviation for Extractables and means the amount of water soluble components (amount of water-solubilized components). Specifically, measurement is carried out by adding 1 g of the water-absorbing resin to 200 g of an 0.9 mass % aqueous saline solution, stirring the solution for 16 hours, and measuring the amount of a dissolved polymer by pH titration (unit: mass %).

(d) "FSC" (ERT440.2-02)

The "FSC" is an abbreviation of Free Swell Capacity and means the ratio of free swelling. Concretely, it is the absorption capacity (unit; [g/g]) measured by immersing 0.20 g of a water-absorbing resin in an aqueous solution of 0.9 mass % of sodium chloride for 30 minutes and carrying out the measurement without dehydration by a centrifuge.

(e) "Residual Monomers" (ERT410.2-02)

The "Residual Monomers" means the amount of monomers remaining in a water-absorbing resin. Specifically, the amount of monomers is a value (unit; ppm by mass)

obtained by measuring, after 0.5 g of a water-absorbing resin is charged to 0.9 mass % saline solution and the resultant is stirred for 2 hours, the amount of monomers eluted in the aqueous solution by using high-pressure liquid chromatography.

(f) "PSD" (ERT420.2-02)

The "PSD" is an abbreviation for Particle Size Distribution and means the particle size distribution measured by sieving classification. The mass average particle diameter (D50) and the particle diameter distribution width can be measured by the same method as in "(1) Average Particle Diameter and Distribution of Particle Diameter" described in European Patent No. 0349240, p. 7, lines $25^{-43}$.

(g) Other Physical Properties of Water-Absorbing Resin Defined in EDANA "pH" (ERT400.2-02): The "pH" means pH of a water-absorbing resin.

"Moisture Content" (ERT430.2-02): The moisture content means the water content percentage of a water-absorbing resin.

"Flow Rate" (ERT450.2-02): The flow rate means the flow down speed of a water-absorbing resin.

"Density" (ERT460.2-02): The density means the bulk specific density of a water-absorbing resin.

"Respirable Particles" (ERT480.2-02): The respirable particles mean the respirable dust of a water-absorbing resin.

"Dust" (ERT490.2-02): The dust means the dust contained in a water-absorbing resin.

(1-5) Liquid Permeability

The "liquid permeability" means the flow of a liquid flowing among particles of swollen gel under a load or without a load. The "liquid permeability" can be measured by SFC (Saline Flow Conductivity) or GBP (Gel Bed Permeability) as a representative measurement method.

The "SFC (saline flow conductivity)" means the liquid permeability of 0.9 g of a water-absorbing resin at a load of 0.3 psi for an aqueous solution of 0.69 mass % of sodium chloride. It is measured according to an SFC testing method described in U.S. Pat. No. 5,669,894.

The "GBP" means the liquid permeability of a water-absorbing resin under a load or free expansion for 0.69 mass % physiological saline solution. It is measured according to a GBP testing method described in WO No. 2005/016393 pamphlet.

(1-6) Heating State of an Apparatus

The "heating state of an apparatus" in the present invention means a state where an apparatus is heated with a heat source such as an electric heater, steam, or hot air, but does not mean a state where the apparatus is kept warm with residual heat after the heat source is turned off. It includes a state where the heat source is turned off for controlling the temperature constant (off). The apparatus means an apparatus employed in the respective steps and examples thereof include a dryer in a drying step and a heating treatment apparatus in a surface treatment step.

(1-7) Interruption of Steps

In the present invention, the "interruption of steps" means a state where a particulated water-containing gel-like crosslinked polymer, a dried material thereof, or a water-absorbing resin powder is substantially absent in an apparatus or not charged to or not discharged out of an apparatus in continuous steps. That is, the "substantially absent state" means that a particulated water-containing gel-like crosslinked polymer, a dried material thereof, or a water-absorbing resin powder, which is in a state of being able to be taken out of an apparatus, is taken out of the apparatus (generally in an amount of not less than 95 mass % in the entire retention capability of the apparatus, preferably not less than 98 mass %, still more preferably not less than 99 mass %, and particularly preferably substantially 100 mass %). A small amount of the particulated water-containing gel-like crosslinked polymer, the dried material thereof, or the water-absorbing resin powder may be deposited, dropped, retained, or scattered in the apparatus. In addition, an idling operation of the apparatus is also included in the "interruption of steps" in the present invention. In the continuous steps, "a state not charged to or discharged out of an apparatus" means a state where a particulated water-containing gel-like crosslinked polymer, a dried material thereof, or a water-absorbing resin powder is stopped in an apparatus and a state where the apparatus is stopped.

(1-8) Continuous Production Such as Continuous Polymerization and Continuous Drying In the present invention, "continuous production such as continuous polymerization and continuous drying" means a state where the water-absorbing resin is continuously charged to and continuously discharged out of an apparatus in the respective steps, the present invention is preferably applied such continuous production (in respective steps of drying, surface-crosslinking, etc.) for an operation time (duration) of preferably not shorter than 24 hours, more preferably not shorter than 240 hours (10 days), and still more preferably not shorter than 720 hours (30 days). The present invention is applied such continuous production (in respective steps of drying, surface-crosslinking, etc.).

(1-9) Others

In this description, "X to Y" showing a range means "not less than X and not more than Y". Additionally, the unit of mass "t (ton)" means "Metric ton" and unless otherwise specified, "ppm" means "ppm by weight" or "ppm by mass". Additionally, " . . . acid (salt)" means " . . . acid and/or a salt thereof" and "(meth)acrylic" means "acrylic and/or methacrylic".

[2] Process for Producing Water-Absorbing Resin (2-1) Polymerization Step

This step is a step of obtaining a water-containing gel-like crosslinked polymer by polymerizing an aqueous solution containing acrylic acid and/or a salt thereof (hereinafter, referred to as an "acrylic acid (salt)" as a main component.

(a) Monomer (Excluding Crosslinking Agent)

A water-absorbing resin to be obtained by the present invention is produced by using, as a raw material (monomer), an aqueous solution containing an acrylic acid (salt) as a main component and generally polymerized in an aqueous solution state. The monomer concentration (solid content concentration) of the aqueous monomer solution is generally 10 to 90 mass % and preferably 20 to 80 mass %. Polymerization with a high monomer concentration (not lower than 35 mass %, still more preferably not lower than 40 mass %, particularly preferably not lower than 45 mass %, and the saturated concentration as the upper limit, still more preferably not higher than 80 mass % and particularly preferably not higher than 70 mass %) is one of most preferable examples.

In the case a monomer is polymerized in an aqueous solution state, if necessary, surfactants, polymer compounds such as a poly(acrylic acid (salt)), starch, cellulose, and polyvinyl alcohol, various kinds of chelating agents, and various kinds of additives may be added in an amount of 0 to 30 mass % relative to the monomer.

The hydrogel obtained by the polymerization of the aqueous solution, preferably has at least partially neutralized acid groups in the polymer from the viewpoint of water absorption properties. The neutralization may be carried out before polymerization (monomer), during polymerization, or after polymerization (hydrogel) of acrylic acid and from the viewpoint of improvement of the productivity of the water-absorbing resin, AAP (absorption capacity under load), SFC (saline flow conductivity), and the like, it is preferable to carry out neutralization before polymerization of acrylic acid. That is, it is preferable to use neutralized acrylic acid (that is, a partially neutralized salt of acrylic acid) as a monomer.

The neutralization ratio of the neutralization is not particularly limited and it is preferably 10 to 100 mol %, more preferably 30 to 95 mol %, still more preferably 50 to 90 mol %, and particularly more preferably 60 to 80 mol % of the acid group. In the case the neutralization ratio is less than 10 mol %, particularly CRC (absorption capacity without load) is sometimes considerably lowered and, therefore, it is not preferable.

In the case an acrylic acid (salt) is used as a main component in the present invention, hydrophilic or hydrophobic unsaturated monomers (hereinafter, sometimes also referred to as "other monomers") may be used besides an acrylic acid (salt). The other monomers is not particularly limited and may include methacrylic acid, maleic acid, maleic anhydride, 2-(meth)acrylamido-2-methylpropanesulfonic acid, (meth)acryloxyalkanesulfonic acid, N-vinyl-2-pyrrolidone, N-vinylacetamide, (meth)acrylamide, Nisopropyl(meth)acrylamide, N,N-dimethyl(meth)acrylamide, 2-hydroxyethyl(meth)acrylate, methoxypolyethylene glycol (meth)acrylate, polyethylene glycol (meth)acrylate, stearyl acrylate, their salts, etc. In the case these other monomers are used, their use amount is not particularly limited as long as the water absorption property of the water-absorbing resin to be obtained is not deteriorated and it is preferably not more than 50 mass % and more preferably not more than 20 mass % relative to the total weight of the monomers.

(b) Salt for Neutralization

A basic substance to be used for neutralizing acrylic acid as a monomer or a polymer (hydrogel) after the polymerization is not particularly limited and is preferably monovalent basic substances, for example, alkali metal hydroxides such as sodium hydroxide, potassium hydroxide and lithium hydroxide, and (hydrogen) carbonate salts such as sodium (hydrogen) carbonate, potassium (hydrogen) carbonate, and the like, and is particularly preferably sodium hydroxide. The temperature at the time of neutralization (neutralization temperature) is also not particularly limited and preferably 10 to 100° C. and more preferably 30 to 90° C. Regarding the neutralization treatment conditions and the like, other than the above-mentioned ones, the conditions and the like, disclosed in WO No. 2006/522181 and U.S. Pat. No. 6,388,000 are preferably employed in the present invention.

(c) Crosslinking Agent (Internal Crosslinking Agent)

In the present invention, from the viewpoint of water absorption properties of the water-absorbing resin to be obtained, it is particularly preferable to use a crosslinking agent (hereinafter, sometimes referred to as an "internal crosslinking agent"). An internal crosslinking agent to be used may be compounds having 2 or more polymerizable double bonds in one molecule and polyfunctional compounds having 2 or more functional groups capable of forming covalent bonds by reaction with a carboxyl group in one molecule. For examples, one or more kinds of polymerizable closslinking agents with the acrylic acid, reactive crosslinking agents with a carboxyl group, and crosslinking agents having both of these properties can be exemplified. Concrete examples are, as a polymerizable crosslinking agent, compounds having at least two polymerizable double bonds in a molecule such as N,N'-methylene bisacrylamide, (poly)ethylene glycol di(meth)acrylate, (polyoxyethylene) trimethylolpropane tri(meth)acrylate, and poly(meth)allyloxyalkanes. Further, examples of the reactive crosslinking agent are covalent-binding crosslinking agents, for example polyglycidyl ether such as ethylene glycol diglycidyl ether, poly alcohols such as propanediol, glycerin, sorbitol and the like, and ion-binding crosslinking agents such as polyvalent metal compounds of aluminum salt and the like. Among these crosslinking agents, from the viewpoint of water absorbent properties, polymerizable crosslinking agents with the acrylic acid, particularly, acrylate type, allyl type, and acrylamide type polymerizable crosslinking agents are preferably used. These internal crosslinking agents may be used alone or two or more kinds of them may be used in combination. The use amount of the internal crosslinking agent is preferably 0.001 to 5 mol %, more preferably 0.005 to 2 mol %, still more preferably 0.01 to 1 mol %, and particularly preferably 0.03 to 0.5 mol % relative to the monomer excluding the crosslinking agent from the viewpoint of physical property.

(d) Other Minor Components

In the present invention, from the viewpoint of color hue stability and residual monomers, the content of protoanemonin and/or furfural in acrylic acid is preferably 0 to 10 ppm, more preferably 0 to 5 ppm, and still more preferably 0 to 1 ppm. For the same reason, the content of an aldehyde component other than furfural and/or maleic acid in acrylic acid is preferably 0 to 5 ppm, more preferably 0 to 3 ppm, still more preferably 0 to 1 ppm, and particularly preferably 0 ppm (under detection limit). Examples of the aldehyde component other than furfural include benzaldehyde, acrolein, acetaldehyde and the like. In order to reduce the residual monomers, the content of acrylic acid dimer is preferably 0 to 500 ppm, more preferably 0 to 200 ppm, and still more preferably 0 to 100 ppm.

In the present invention, from the viewpoint of polymerization stability, it is preferable to include methoxyphenols in the unsaturated monomers and it is more preferable to include p-methoxyphenol. The content of methoxyphenols is preferably 1 to 250 ppm, more preferably 5 to 200 ppm, still more preferably 10 to 160 ppm, and particularly preferably 20 to 100 ppm relative to the monomer (acrylic acid).

(e) Other Components in Aqueous Monomer Solution

In order to improve various physical properties of the water-absorbing resin to be obtained by the present invention, the following substances may be added as arbitrary components to the aqueous monomer solution. That is, a water-soluble resin or a water-absorbing resin such as starch, a polyacrylic acid (salt), polyvinyl alcohol, or polyethylene imine may be added in an amount of, for example, 0 to 50 mass %, preferably 0 to 20 mass %, more preferably 0 to 10 mass %, and still more preferably 0 to 3 mass % to the monomer. Further, additives such as various kinds of foaming agents (carbonates, azo compounds, air bubbles, etc.), surfactants, various kinds of chelating agents, hydroxycarboxylic acids, and reducing inorganic salts may be added in an amount of, for example, 0 to 5 mass % and preferably 0 to 1 mass % relative to the monomer.

Among them, in the case of aiming at suppression of coloration with the time (improvement of color hue stability at the time of long time storage under high temperature and high humidity) and improvement of urine resistance (gel deterioration prevention) of the water-absorbing resin, a chelating agent, a hydroxycarboxylic acid, and a reducing inorganic salt are preferably used and a chelating agent is particularly preferably used. The use amount in this case is preferably 10 to 5000 ppm, more preferably 10 to 1000 ppm, still more preferably 50 to 1000 ppm, and particularly preferably 100 to 1000 ppm relative to the water-absorbing resin. The compounds disclosed in WO No. 2009/005114 and EU Patent Application Publication Nos. 2057228 and 1848758 may be used for the chelating agent, hydroxycarboxylic acid, and reducing inorganic salt.

(f) Polymerization Initiator

A polymerization initiator to be used for the present invention is not particularly limited and can be selected properly in accordance with the polymerization mode. Examples of the polymerization initiator may include a heat decomposition type polymerization initiator, a photodecomposition type polymerization initiator, a redox type polymerization initiator, and the like. Examples of the heat decomposition type polymerization initiator may include persulfate such as sodium persulfate, potassium persulfate, and ammonium persulfate; peroxides such as hydrogen peroxide, tert-butyl peroxide, and methyl ethyl ketone peroxide; azo compounds such as 2,2'-azobis(2-amindinopropane)dihydrochloride, 2,2'-azobis[2(2-imidazolin-2-yl)propane]dihydrochloride, and the like. Examples of the photodecomposition type polymerization initiator may include benzoin derivatives, benzyl derivatives, acetophenone derivatives, benzophenone derivatives, azo compounds, and the like. Examples of the redox type polymerization initiator may include the above-mentioned persulfate or peroxides in combination with reducing compounds such as L-ascorbic acid and sodium hydrogen sulfite. Further, combination use of a heat decomposition type polymerization initiator and a photodecomposition type polymerization initiator can also be exemplified as a preferable embodiment. The use amount of those polymerization initiators is preferably 0.0001 to 1 mol % and more preferably 0.001 to 0.5 mol % relative to the monomer. In the case the use amount of a polymerization initiator exceeds 1 mol %, it may cause coloration of the water-absorbing resin and, therefore, it is not preferable. On the other hand, if the use amount of a polymerization initiator is below 0.0001 mol %, it may possibly increase the residual monomer amount and, therefore, it is not preferable.

In place of use of the polymerization initiator, polymerization may be carried out by irradiation with an active energy beam such as radiation beam, electron beam, or ultraviolet rays and also polymerization may be carried out by employing the active energy beam and a polymerization initiator in combination.

(g) Polymerization Method (Crosslinking Polymerization Step)

In the present invention, from the viewpoint of water absorption properties of a water-absorbing resin to be obtained and ease of polymerization control in the case of polymerization of the aqueous monomer solution, and the like, generally, aqueous solution polymerization or reverse phase suspension polymerization is employed, and aqueous solution polymerization is preferable and continuous aqueous solution polymerization is more preferably employed. Among them, continuous aqueous solution polymerization is preferably employed for production of a water-absorbing resin in a huge scale with a large production amount for one line. The production amount is 0.5 [t/hr] or higher, more preferably 1 [t/hr] or higher, still more preferably 5 [t/hr] or higher, and particularly preferably 10 [t/hr] or higher.

Examples of a preferable embodiment of the continuous aqueous solution polymerization include continuous belt polymerization (U.S. Pat. Nos. 4,893,999 and 6,241,928, US Patent Application Publication No. 2005/215734, etc.) and continuous kneader polymerization (U.S. Pat. Nos. 6,987,151, 670,141, etc.).

One of most preferable examples of the continuous aqueous solution polymerization is high temperature starting polymerization at a polymerization starting temperature of not lower than 30° C., preferably not lower than 35° C., more preferably not lower than 40° C., still more preferably not lower than 50° C., and particularly preferably not lower than 60° C. (upper limit is boiling point) or high monomer concentration polymerization with a monomer concentration of not lower than 35 mass %, preferably not lower than 40 mass %, and particularly preferably not lower than 45 mass % (upper limit is the saturated concentration). The polymerization starting temperature is defined in accordance with the liquid temperature of an aqueous monomer solution immediately before the solution is supplied to a polymerization apparatus, the conditions, and the like, disclosed in U.S. Pat. Nos. 6,906,159, 7,091,253, etc. can be employed preferably for the present invention.

From the viewpoint of improvement of physical property of the water-absorbing resin to be obtained and drying efficiency, it is preferable to evaporate water at the time of polymerization and obtain a water-absorbing resin with a higher solid content concentration. The increase degree of the solid content from the aqueous monomer solution (solid content of hydrogel after polymerization—solid content of monomer before polymerization) is preferably not less than 1 mass %, more preferably 2 to 40 mass %, and still more preferably 3 to 30 mass %. The increase degree is preferably within a range of giving a water-containing gel-like crosslinked polymer containing not more than 80 mass % of solid content.

The polymerization can be carried out in atmospheric air; however, from the viewpoint of prevention of coloration, it is preferable to carry out the polymerization in an inert gas atmosphere of nitrogen, argon, and the like (e.g., with not more than 1% by volume of oxygen concentration). It is also preferable to carry out the polymerization after replacing the dissolved oxygen in a monomer or a solution containing a monomer with an inert gas (e.g., dissolved oxygen concentration; less than 1 mg/L). The polymerization can be carried out under any pressure; that is, under reduced pressure, under normal pressure, or under pressurization.

(2-2) Finely Crushing Step of Water-Containing Gel-Like Crosslinked Polymer (Gel-Crushing Step)

This step is a step of finely crushing a water-containing gel-like crosslinked polymer obtained in the polymerization step to obtain a particulated water-containing gel-like crosslinked polymer (hereinafter, referred to as a "particulated hydrogel").

The hydrogel obtained in the polymerization step may be dried as it is, but in order to solve the above-mentioned problems, the hydrogel may be gel-crushed, if necessary, preferably during the polymerization or after the polymerization by a crusher (a kneader, a meat chopper, a cutter mill, etc.) to be particulate. That is, between the polymerization step by the continuous belt polymerization or the continuous kneader polymerization and the drying step, a step of finely crushing of the hydrogel (hereinafter, also referred to as "gel-crushing") may be added further. In addition, even in the case the gel is finely crushed by dispersion in a solvent at the time of polymerization such as reverse-phase suspension polymerization, the finely crushing step (finely crushing during polymerization) is included in the finely crushing step of the present invention, and the finely crushing is preferably carried out using a crusher.

The temperature of the hydrogel at the time of gel-crushing is kept at or increased to preferably 40 to 95° C. and more preferably 50 to 80° C. from the viewpoint of physical properties. The mass average particle diameter (D50) of the particulated hydrogel after the gel-crushing is preferably 0.5 to 4 mm, more preferably 0.3 to 3 mm, and still more preferably 0.5 to 2 mm. If the mass average particle diameter (D50) of the particulated hydrogel is within the above-mentioned range, drying is efficiently carried out and, therefore, it is preferable. The ratio of the particulated hydrogel having a particle diameter of not smaller than 5 mm is preferably 0 to 10 mass % and more preferably 0 to 5 mass % in the entire particulated hydrogel. Herein, the particle diameter of the particulated hydrogel is measured by a wet classification method described in paragraph [0091] in JP-A-2000-63527.

(2-3) Drying Step

The drying step is a step of drying a particulated water-containing gel-like crosslinked polymer obtained in finely crushing step during the polymerization or after the polymerization.

(a) Dryer

A dryer to be used in the present invention is preferably an air ventilating belt type dryer (belt type dryer) and also, if necessary, one or more kinds of a heat conduction and heat transfer type dryer, a radiation heat transfer type dryer, a hot air heat transfer type dryer, an induction heating type dryer, etc. may be used and from the viewpoint of quick drying, a hot air heat transfer type dryer (hereinafter, referred to as a hot air dryer) is preferable. Examples of the hot air dryer include an air ventilating belt (band) type, air ventilating circuit type, air ventilating vertical type, parallel flow belt (band) type, air ventilating tunnel type, air ventilating groove stirring type, fluidized bed type, current type, spraying type dryers and the like, and in the present invention, from the viewpoint of the physical property control, an air ventilating belt type dryer is preferable. It is possible to use another dryer in combination, but it is preferable to carry out drying by solely the air ventilating belt type dryer (belt type dryer).

Examples of the heat source include an electric heater, and various kinds of heated gases such as steam and hot air. Heated steam (not lower than 100° C.) is particularly preferably used as a heat source. The heated steam is recycled and reheated through a heat exchanger if necessary, and used in the drying step of the water-absorbing resin or in another step. The heating temperature may be constant or fluctuated.

The drying temperature is in a temperature range (hot air temperature) of generally 100 to 250° C., preferably 100 to 220° C., more preferably 120 to 200° C., and particularly preferably 150 to 190° C. It is more efficient that the velocity of the hot air passing in a drying chamber is higher in a range of scarcely blowing out the polymer and the velocity is preferably 0.1 to 5 [m/s] and more preferably 0.5 to 3 [m/s]. If the velocity is below 0.1 [m/s], it takes such a long time to dry out to a prescribed moisture content that a huge dryer is required. On the other hand, if the velocity exceeds 5 [m/s], the amount of the polymer flying out of the drying chamber is increased and stable operation becomes difficult. The drying time (the time from charging of the particluated water-containing gel-like crosslinked polymer to the dryer to discharge of the same particluated water-containing gel-like crosslinked polymer in form of a dried material out of the dryer) depends on the surface area and moisture content of the polymer, the type of the dryer, and the air blow quantity and is selected to give an intended moisture content. For example, the drying time is properly selected in a range of preferably 1 minute to 1 hour.

The present invention is applied for huge scale continuous drying with a belt length of the dryer in a range of 5 to 100 m, further 10 to 70 m, and particularly 20 to 60 m. The width of the belt is not particularly limited and it is properly determined in a range of generally 0.5 to 10 m and further 1 to 5 m. The ratio between the width direction and the longitudinal direction may be determined in accordance with the purpose, but it is preferably longer in the longitudinal direction (proceeding direction) than in the width direction and the ratio is properly determined in a range of generally 3 to 500 times and further 5 to 100 times.

The drying in the present invention is preferably carried out on a continuous air ventilating belt and examples of the air ventilating belt include a metal net (e.g., meshes of 1000 to 45 μm) and a punching metal and a punching metal is preferably used. The shape of holes of a punching metal may be various and examples thereof include round holes, elliptic holes, rectangular holes, hexagonal holes, long round holes, long rectangular holes, diamond holes, cross holes, and a plurality of these holes in combination and the arrangement of the holes may be in zigzag or in parallel arrangement. The belt may have holes formed three-dimensionally like louvers but preferably have holes in a flat structure. The pitch direction of the belt may be vertical, transverse, or slanting to the belt proceeding direction and may be a combination of these. The size of the holes and hole ratio of the punching metal will be described later.

The conveying speed of the particulated water-containing gel-like crosslinked polymer on the air ventilating belt may be properly adjusted in accordance with the belt width, the belt length, the production amount, and the drying time and from the viewpoint of the load to the belt driving apparatus, durability, and the like, it is preferably 0.3 to 5 [m/min], more preferably 0.5 to 2.5 [m/min], still more preferably 0.5 to 2 [m/min], and particularly preferably 0.7 to 1.5 [m/min].

In order to achieve the present invention, it is preferable to change the temperature, dew point, and air blow quantity in multi-stages and, therefore, the air ventilating belt type dryer preferably has not less than 5 chambers, particularly not less than 6 chambers, and further not less than 8 chambers. The upper limit may be properly set in accordance with the scale or the like, and generally about 20 chambers suffice.

(b) Surface Occupancy

In the production process of the present invention, in the case an air ventilating band dryer is used, the surface occupancy on the belt is generally 85 to 100%, preferably 87 to 100%, more preferably 87 to 99%, particularly preferably 90 to 98%, and most preferably 93 to 97%. The surface occupancy is defined as the area ratio (percentage) of the layered material of the particulated hydrogel occupying the air ventilating belt face to the air ventilating belt area (A) in the initial period of the drying step. The air ventilating belt area (A) includes the areas of the holes. The area (B) of the air ventilating belt face on which the layered material of the particulated hydrogel in the initial drying period occupies is defined by the occupying area of the layered material of the particulated hydrogel in the section. The surface occupancy (B/A×100(%)) is defined by the air ventilating belt area (A) that is defined aforementioned and the area (B) occupied by the layered material of the particulated hydrogel. If the surface occupancy exceeds 99% or less than 85%, it is found that the physical properties of a water-absorbing resin tend to be deteriorated and the dropping and scattering ratio, drying efficiency, and continuous drying property tend to be lowered. Unoccupied places on the belt may be properly determined and parts where no hydrogel is layered may be formed in certain set positions in the center part, both end parts, and middle parts and preferably a prescribed region where no hydrogel is set is formed in both end parts.

(c) Hole Ratio and Holes

In the production process of the present invention, in the case an air ventilating band dryer is used, the hole ratio of the punching metal is preferably 15 to 50%, more preferably 20 to 45%, and particularly preferably 25 to 40%. The hole ratio is determined in accordance with the holes, pitches (P) and the like, and in the case there is no hole in a certain prescribed region, for example, the punching metal has rims, the hole ratio is defined based on the area including the region. If the hole ratio is out of the above-mentioned range, it is found that the physical properties of a water-absorbing resin tend to be deteriorated and the drying efficiency and continuous drying property tend to be lowered.

The area of one hole (in the case where there are a plurality of types of holes, the area is defined as an average opening area) is preferably larger than the cross-sectional area of one particle of the particulated hydrogel, more preferably in a range of 2 to 100 times as large, and still more preferably in a range of 4 to 50 times as large. The maximum opening distance of each hole (e.g., the diameter in the case of a circle, or the longer diameter in the case of an ellipse) is preferably larger than the mass average particle diameter of the particulated hydrogel, more preferably in a range of 2 to 100 times as large, and still more preferably in a range of 4 to 50 times as large. The average opening area of the holes is 5 to 500 mm$^2$, preferably 10 to 100 mm$^2$, and particularly preferably 15 to 50 mm$^2$. In the case the area is smaller than the above-mentioned range, the drying efficiency is lowered and in the case it is larger, the yield of the dried material is lowered and, therefore, these cases are not preferable.

(d) Resin Solid Content

As described above, in the polymerization step in the production process of the present invention, continuous kneader polymerization or continuous belt polymerization, which is carried out while evaporating water, is preferable. In this polymerization step, the increase degree of the solid content (the difference between the solid content of the aqueous monomer solution and the gel solid content) is not less than 1 mass %, further not less than 2 mass %, and particularly not less than 5 mass % and owing to the solid content increase, the water-absorbing resin with high physical properties can be obtained with high productivity and low energy. In the drying step, similarly, increase of the resin solid content not only reduces energy but also causes a preferable effect on decrease of adhesion to the dryer.

From the viewpoint of solid content increase in the drying step, prevention of adhesion of the hydrogel to the dryer, particle size control of a product, and the like, the water-absorbing resin fine particles obtained in the classification step can be recycled to the particulated water-containing gel-like crosslinked polymer before drying. The solid content of the particulated water-containing gel-like crosslinked polymer before introduction into the drying step is preferably not less than 45 mass %. The particulated water-containing gel-like crosslinked polymer is dried in a scale of 1 [t/hr] or more. The resin solid content can be controlled based on the monomer concentration, water evaporation at the time of polymerization, recycling of the fine powder, and the like and increase of the resin solid content can not only reduce the energy but also adhesion to the dryer.

(2-4) Pulverizing Step and Classification Step (Particle Size Adjustment after Drying)

These steps are steps for pulverizing and classifying the dried material obtained in the drying step to obtain a water-absorbing resin powder. The water-absorbing resin powder is a water-absorbing resin before the water-absorbing resin is subjected to the following surface-crosslinking treatment. The dried material obtained in the drying step can be used as a dried powder as it is, but the particulated hydrogel may possibly be agglomerated at the time of drying to form block-like agglomerates. This phenomenon is observed particularly in a band dryer and pulverizing or rough crushing (break into small pieces) is needed. Further, in order to improve the physical properties in the surface-crosslinking step described later, it is preferable to control the water-absorbing resin powder to have a specified particle size. The particle size may be properly controlled not only in the pulverizing step and classification step but also in the polymerization step (particularly, reverse-phase suspension polymerization), the fine powder recovery step, the granulation step, etc. Hereinafter, the particle size is defined by a standard sieve (JIS Z8801-1 (2000)).

A pulverizer to be used in the pulverizing step is not particularly limited and conventionally known pulverizers may be used. Specific examples thereof include a roll mill, a hammer mill, a roll granulator, a jaw crusher, a gyrectory crusher, a cone crusher, a roll crusher, a cutter mill, etc. Among them, a multi-stage roll mill or a roll granulator is preferably used from the viewpoint of particle size control. In the classification step, various kinds of classification apparatuses such as sieving classification and air current classification can be used.

The classification step in the present invention is carried out inevitably before surface-crosslinking and/or after surface-crosslinking, preferably before surface-crosslinking, and still more preferably carried out twice in total before surface-crosslinking and/or after surface-crosslinking.

From the viewpoint of improvement of physical properties of a water-absorbing resin to be obtained in this step, it is preferable to control the particle size to be in the following range. That is, the mass average particle diameter (D50) of the water-absorbing resin powder (before surface-crosslinking) is preferably 200 to 600 more preferably 200 to 550 µm, still more preferably 250 to 500 µm, and particularly preferably 350 to 450 µm. The ratio of fine particles which pass through a sieve with meshes of 150 µm (JIS standard sieve) is preferably 0 to 5 mass %, more preferably 0 to 3 mass %, and still more preferably 0 to 1 mass % relative to in the entire water-absorbing resin powder. The ratio of coarse particles which do not pass through a sieve with meshes of 850 µm (JIS standard sieve) is preferably 0 to 5 mass %, more preferably 0 to 3 mass %, and still more preferably 0 to 1 mass % relative to the entire water-absorbing resin powder. The particle size is measured by a method disclosed in WO No. 2004/69915 and EDANA-ERT420.2.-02 (Particle Size Distribution).

(2-5) Surface Treatment Step

In the present invention, a step for reforming the periphery of particle surface for the water-absorbing resin powder (particles) described particle size is called as a surface treatment step. Herein, the "surface treatment" may be surface-crosslinking and also addition of various kinds of additives and polymers to the particle surface and preferably, surface-crosslinking by a thermal reaction is indispensably carried out. The surface treatment other than surface-crosslinking may be addition of a water-soluble or water-insoluble polymer, a lubricant, a chelating agent, a deodorant, an antibacterial agent, water, a surfactant, water-insoluble fine particles, an antioxidant, a reducing agent, etc. These agents may be added and mixed in an amount of preferably 0 to 30 mass % and more preferably 0.01 to 10 mass % to the water-absorbing resin powder or water-absorbing resin particles after surface-crosslinking. These agents may be mixed and heated up to the above-mentioned upper limit in place of the following surface-crosslinking agent. Hereinafter, a surface-crosslinking step is explained as a representative and the following respective steps of mixing, heating, and stopping can be properly be applied for the surface treatment step, which is a superordinate concept.

(a) Mixing Step (Surface-Crosslinking Step)

In the present invention, in order to improve the water absorption performance, preferably a surface-crosslinking step is further involved. In the present invention, coloration is scarcely caused and a whiter water-absorbing resin can be obtained by the surface-crosslinking treatment. The following respective steps can be applied preferably for surface-crosslinking of a water-absorbing resin, particularly for high temperature surface-crosslinking.

The surface-crosslinking step in the present invention is composed of a step of mixing a water-absorbing resin powder with a surface-crosslinking agent, a step of heating treatment for the mixture, and a cooling step carried out if necessary.

(Covalent Bonding Surface-Crosslinking Agent)

A surface-crosslinking agent to be used for the present invention is not particularly limited and various kinds of organic and inorganic surface-crosslinking agents can be mentioned. Particularly, an organic surface-crosslinking agent alone or combination use of an organic surface-crosslinking agent and an ion bonding surface-crosslinking agent is preferable. A covalent bonding surface-crosslinking agent is preferably used as the organic surface-crosslinking agent, preferable examples to be used are dehydration reactive surface-crosslinking agents such as polyhydric alcohol compounds, epoxy compounds, polyamine compounds and their condensation products with haloepoxy compounds, oxazoline compounds (mono-, di-, or poly-)oxazolidinone compounds, and alkylene carbonate compounds. Particularly dehydration reactive surface-crosslinking agents such as a polyhydric alcohol compound, an alkylene carbonate compound, and an oxazolidinone compound, which require high temperature reaction are preferably used. More concretely, examples are compounds exemplified in U.S. Pat. Nos. 6,228,930, 6,071,976, 6,254,990, etc. Examples are dehydration esterification reactive surface-crosslinking agents include polyalcohol compounds such as mono-, di-, tri-, or tetra-propylene glycol, 1,3-propanediol, glycerin, 1,4-butanediol, 1,3-butanediol, 1,5-pentanediol, 1,6-hexanediol and sorbitol; epoxy compounds such as ethylene glycol diglycidyl ether and glycidol; alkylene carbonate compounds such as ethylene carbonate; oxetane compounds; cyclic urea compounds such as 2-imidazolidinone; and the like. One or more kinds of covalent surface-crosslinking agents (particularly, dehydration reactive surface-crosslinking agents) can be used in combination. The use amount of the surface-crosslinking agents may be properly determined in a range of preferably 0.001 to 10 parts by mass and more preferably 0.01 to 5 parts by mass relative to 100 parts by mass of the water-absorbing resin powder.

(Ion Bonding Surface-Crosslinking Agent)

In the present invention, from the viewpoint of improvement of physical properties such as liquid permeability, an inorganic surface-crosslinking agent can be used other than the organic surface-crosslinking agent. Examples usable as the inorganic surface-crosslinking agent is not particularly limited and may include divalent or higher, preferably, trivalent to tetravalent polyvalent metal salts (organic salts and inorganic salts) or hydroxides. Concretely, polyvalent metals to be used are aluminum, zirconium, etc., and aluminum lactate and aluminum sulfate are usable. These inorganic surface-crosslinking agents may be used simultaneously with or separately from the organic surface-crosslinking agent. The surface-crosslinking with polyvalent metals is exemplified in International Publication Nos. 2007/121037, 2008/09843, and 2008/09642, in U.S. Pat. Nos. 7,157,141, 6,605,673, and 6620889, in US Patent Application Publication Nos. 2005/0288182, 2005/0070671, 2007/0106013, 2006/0073969, etc. One or more kinds of ion bonding surface-crosslinking agents can be used in combination. The use amount may be properly determined in a range of preferably 0.001 to 10 parts by mass and more preferably 0.01 to 5 parts by mass relative to 100 parts by mass of the water-absorbing resin powder.

In the present invention, from the viewpoint of improvement of physical properties such as liquid permeability, a polyamine polymer may be used simultaneously or separately in addition to the organic surface-crosslinking agent. A polyamine polymer having a mass average molecular weight of about 5000 to 1000000 is particularly preferably used, and examples are exemplified in U.S. Pat. No. 7,098,284, WO Nos. 2006/082188, 2006/082189, 2006/082197, 2006/111402, 2006/111403, 2006/111404, etc.

The present invention can provide a water-absorbing resin with high whiteness even by high temperature heating or heating treatment with air (hot air) which conventionally causes intense coloration. In the case of aiming at providing particularly a sanitary material (especially a paper diaper), it is preferable to improve the absorption capacity under load (AAP) described later to the following range, preferably not less than 20 g/g by a surface-crosslinking treatment.

At the time of mixing the surface-crosslinking agent, water is preferably used as a solvent. The use amount of water may be properly determined in a range of preferably 0.5 to 20 parts by mass and more preferably 0.5 to 10 parts by mass relative to 100 parts by mass of the water-absorbing resin powder. A hydrophilic organic solvent may be used in combination if necessary, other than water, and its use amount may be properly determined in a range of preferably 0 to 10 parts by mass and more preferably 0 to 5 parts by mass relative to 100 parts by mass of the water-absorbing resin powder.

Further, at the time of mixing a surface-crosslinking agent solution, a water-insoluble fine particle powder and a surfactant are allowed to coexist to an extent that the effect of the present invention is not hindered. The types, the use amount, and the like, of the water-insoluble fine particle powder and surfactant are described in, for example, U.S. Pat. No. 7,473,739 etc. and the use amount may be properly determined in a range of preferably 0 to 10 parts by mass, more preferably 0 to 5 parts by mass, and still more preferably 0 to 1 part by mass relative to 100 parts by mass of the water-absorbing resin powder.

(b) Heating Treatment Step

In the surface-crosslinking step, after the water-absorbing resin powder and a surface-crosslinking agent are mixed, the mixture is preferably subjected to a heating treatment and thereafter to a cooling treatment if necessary. A conventionally known dryer is used for the heating treatment. The heating temperature (which is a heat medium temperature or a material temperature, particularly a material temperature) at the time of the heating treatment may be properly determined in accordance with the type, amount, and the like, of the surface-crosslinking agent to be used and it is preferably 70 to 300° C., more preferably 120 to 250° C., still more preferably 150 to 250° C., and particularly preferably 170 to 230° C. In the case a dehydration reactive surface-crosslinking agent is used, the heating temperature is preferably 150 to 250° C. and more preferably 170 to 230° C. In the case the treatment temperature is lower than 70° C., the heating treatment time is extended and it results in decrease of the productivity and further it becomes impossible to form a uniform surface-crosslinked layer and, therefore, it is not preferable. In the case the treatment temperature exceeds 300° C., the water-absorbing resin powder is deteriorated and, therefore, it is not preferable. The heating time for the heating treatment is preferably in a range of 1 minute to 2 hours. The heating treatment can be carried out in a common dryer or a heating furnace. The methods of surface-crosslinking described in EP Patent Nos. 0349240, 0605150, 0450923, 0812873, 0450924, 0668080, Japan Patent Application Publication Nos. 7-242709, 7-224304, U.S. Pat. Nos. 5,409,771, 5,597,873, 5,385,983, 5,610,220, 5,633,316, 5,674,633, 5,462,972, WO Nos. 99/42494, 99/43720, 99/42496, etc. can be employed preferably in the present invention.

(Heating Treatment Apparatus)

Various kinds of heating treatment apparatuses such as a fluidized bed heating treatment apparatus, a belt type heating treatment apparatus, a paddle type heating treatment apparatus, a disk type heating treatment apparatus, a hot air heating treatment apparatus, an infrared heating treatment apparatus can be used as the heating treatment apparatus of the present invention. Among them, a paddle type heating treatment apparatus is preferable and a disk type heating treatment apparatus is particularly preferable. Specific examples thereof include a Bepex-heating treatment apparatus and a Nara-heating treatment apparatus. In this description, for convenience, the term "heating treatment apparatus" is employed, but it is same as a dryer. The heating treatment can be carried out by heating a jacket or blowing hot air in the heating treatment apparatus itself. A dryer connected successively, for example, a box type dryer, a rotary tubular furnace, or a heatable screw is also proper.

(c) Cooling Step

This step is a step carried out arbitrarily after the heating treatment step. In the case a dehydration reactive crosslinking agent made from a polyhydric alcohol compound, an alkylene carbonate compound, and an oxazolidinone compound, which require high temperature reaction, is used in the heating treatment step, the cooling step is preferably carried out.

A cooling apparatus to be used in the cooling step is not particularly limited and an apparatus having the same configuration as the apparatus used for the heating treatment step can be used. That is, the apparatus may be the transverse type continuous stirring apparatus or the apparatus described in U.S. Pat. No. 7,378,453 etc. For example, a biaxial stirring apparatus in which cooling water is circulated in the inner wall or other heat transfer surfaces and the like, can be used. The temperature of the cooling water is adjusted to be lower than the heating treatment temperature in the surface treatment step and may be properly determined in a range of preferably not lower than 25° C. and lower than 70° C.

(2-6) Storage Step

Figure 1:
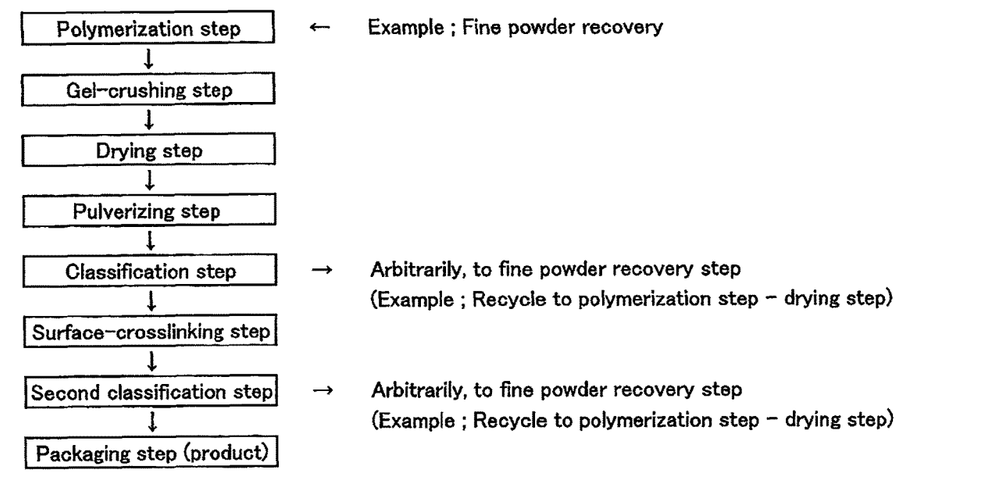
FIG. 1 is a schematic view showing the typical continuous production flow of a water-absorbing resin.

The process for producing a water-absorbing resin in the present invention is characterized in that while some of continuous steps are kept running, other continuous steps are interrupted. That is, the process for producing a water-absorbing resin involves a plurality of joined continuous steps; a polymerization step of polymerizing an aqueous unsaturated monomer solution, a drying step of drying a particulated water-containing gel-like crosslinked polymer obtained in a crushing step during the polymerization or after the polymerization, a pulverizing step after the drying, a classification step after the drying, and a surface treatment step for the water-absorbing resin powder after the classification step (e.g. see FIG. 1) and is characterized in that with some of the above steps kept running, the other steps are interrupted, and subsequently all the steps are restarted.

The process for producing the water-absorbing resin involves a large number of continuously carried out steps such as a polymerization step, a finely crushing step, a drying step, a pulverizing step, a classification step. At the time of periodic maintenance and a temporal trouble (an operation trouble in some steps), it is necessary to stop all of the steps and to stop the continuous production flow of the water-absorbing resin or hydrogel thereof. The operation is restarted after these countermeasures are taken, and in such a case, because the quality of the water-absorbing resin to be obtained is not stabilized or excess energy is needed to restart the operation, apparatuses sometimes get out of order and the operation may be stopped again. Further, colored foreign matters (mainly a discolored matter of the water-absorbing resin) are sometimes mixed at the time of restarting of the operation.

To solve the above-mentioned problems, the inventors of the present invention have paid attention to a method of stopping the respective steps and finally have found that the above-mentioned problems can be solved by interrupting some of continuous steps while the other continuous steps are kept running, among a plurality of joined continuous steps. That is, it was made possible to carry out stable and continuous operation without stopping the entire production process by carrying out operation in the above-mentioned manner. Herein, the continuous step to be interrupted is preferably the polymerization step or the drying step, or the classification step or the pulverizing step. The steps to be carried out subsequently to these steps, e.g. the surface treatment step and the like, as it is, can be carried out continuously. In the present invention, the continuous steps before the interrupted step can also be run.

In the above-mentioned case where the steps before the continuous steps to be interrupted are kept running, it is preferable to carry out a storage step of temporarily storing the water-absorbing resin to be charged to the steps to be interrupted. The storage step means a hopper or a silo installed between the continuous steps and other continuous steps. The size and the filling ratio of the hopper or the silo will be described later.

In the case a hopper is installed in the middle of respective steps, a preferable installation embodiment is as follows. That is, an un-filled hopper or a hopper with a low filling ratio for temporarily storing the water-absorbing resin is installed between the drying step and either the pulverizing step or the classification step after the drying, and temporarily store the water-absorbing resin in the installed hopper after the drying at the time of stopping the pulverizing step or the steps after the classification step. In addition, an un-filled hopper or a hopper with a low filling ratio for temporarily storing the water-absorbing resin is installed between the classification step and the surface treatment step to temporarily store the water-absorbing resin after the classification at the time of stopping the steps after the surface treatment step.

The time from stopping to starting of the respective steps (the interruption period in the present invention) is preferably not shorter than 0.5 hours, more preferably not shorter than 0.5 hours and within 100 days, still more preferably not shorter than 1 hour and within 50 days, particularly preferably not shorter than 5 hours and within 20 days, and most preferably not shorter than 10 hours and within 15 days.

(Hopper)

Examples of a hopper and a silo preferable for the storage step are described in the above-mentioned Patent Document 4 (WO No. 2009/113672), Patent Document 8 (U.S. Pat. No. 6,727,345), and Patent Document 10 (U.S. Pat. No. 6,817,557).

Patent Documents 4, 8, and 10 disclose a hopper or a silo in the production process of a water-absorbing resin, but do not disclose installation of a hopper or silo with a low filling ratio, or an un-filled hopper or silo which is employed in the present invention.

The filling ratio of the hopper or silo is preferably 0 to 50%, more preferably 0 to 30%, and still more preferably 0 to 10%. The capacity of the hopper or silo is preferably enough for the production quantity of the water-absorbing resin per hour, for example, not smaller than 20%, not smaller than 50%, not smaller than 100%, not smaller than 500%, or not smaller than 1000% of production quantity per hour. For example, in the case the water-absorbing resin is continuously produced at 1 [t/hr], a large volume storage step (a hopper or a silo) with a capacity of 1 t in the case of 100% and 10 t in the case of 1000% is preferable. It is preferable to heat the hopper (the atmosphere temperature in the hopper) to a prescribed temperature, that is, to 40° C. or higher. The heating temperature is preferably not lower than 60° C. and most preferably 80 to 140° C. It is also preferable that the inside of the hopper is in a reduced pressure state. The shape of the hopper is an inverse circular truncated conical shape or an inverse truncated pyramidal shape and the reducing ratio of the hopper (the area ratio between a transverse cross sectional area of the trunk part and the opening part) is preferably 35 to 80%, more preferably 40 to 70%, and still more preferably 45 to 60%. The material of the hopper is generally a stainless steel and the surface roughness (Rz) of the inner face of the hopper is preferably not more than 800 nm, more preferably not more than 600 nm, and still more preferably not more than 200 nm. The hopper may be subjected to static electricity removal treatment.

(2-7) Fine Powder Recycling Step

The fine powder recycling step in the present invention is a step of recycling a fine powder (particularly, a fine powder containing particles not larger than 150 µm as a main component in an amount of particularly not less than 70 mass %) obtained by drying and if necessary pulverizing and classification to the polymerization step or the drying step after separation as it is or after hydration. For example, methods described in US Patent Application Publication No. 2006/247351 and U.S. Pat. No. 6,228,930, etc. can be employed.

The particle size can be controlled by adding the recycled fine powder and additionally, a high solid content, which is indispensable in the present invention, can be easily achieved by adding a water-absorbing resin powder and further, and an addition of the fine powder makes separation of the water-absorbing resin from a drying belt after drying easy and, therefore, it is preferable.

Regarding a water-absorbing resin obtained by a production process involving a fine powder recycling step, in a conventional production process, because of uneven drying due to the addition of the fine powder, increase of residual monomers, decrease of absorption capacity, and the like, it has been difficult to obtain a water-absorbing resin with high physical properties. On the other hand, in the production process of the present invention, particularly in the case the process for producing a water-absorbing resin involves the fine powder recycling step, the process is excellent in the effect of preventing physical property deterioration and preventing coloration. That is, it is preferable that the solid content of the hydrogel is increased to not less than 45 mass %, not less than 50 mass %, not less than 55 mass %, and not less than 60 mass % by evaporating water or adding a water-absorbing resin fine powder in the polymerization step. The increase of the solid content from the monomer (solid content of hydrogel after polymerization—mass % of monomer before polymerization) is preferably not less than 1 mass %, further 2 to 40 mass %, and particularly preferably in the range of 3 to 30 mass %. It is also preferable to add a step of recycling the water-absorbing resin fine powder after drying or its moisturized product to the polymerization step or drying step.

(2-8) Other Step

Besides the above-mentioned continuous steps, if necessary, a surface treatment step for a polyvalent metal salt, a recycling step of the evaporated monomer, a granulation step, a fine powder removal step, etc. may be provided. In order to cause an effect for color stabilization with time, prevent gel deterioration and the like, the following additives may be added to some or all of the respective steps if necessary. The production process of the present invention preferably involves the fine powder recycling step.

During polymerization or after polymerization, a water-soluble or water-insoluble polymer, a lubricant, a chelating agent, a deodorant, an antibacterial agent, water, a surfactant, water-insoluble fine particles, an antioxidant, a reducing agent, etc. may be added and mixed in an amount of 0 to 30 mass % and further about 0.01 to 10 mass % to the water-absorbing resin particles. These additives may also be used as a surface treatment agent.

One or more steps such as a conveying step, a storage step, a packaging step, and an addition step of adding other additives (fine particles, a deodorant, an antibacterial agent, etc.) may also be preferably carried out.

These steps are described in Patent Documents 1 to 10 etc.

(Stopping of Heating)

The respective steps are stopped while being kept in a heated state to preferably not lower than 40° C., more preferably not lower than 50° C., and still more preferably not lower than 60° C. The upper limit of the heating temperature is preferably not higher than 140° C., more preferably not higher than 120° C., and particularly preferably not higher than 100° C. in terms of the cost and coloration.

In the present invention, preferably the drying step and/or the surface treatment step (especially the surface-crosslinking step) among the respective steps for producing the water-absorbing resin are stopped in a heated state; and more preferably, the drying step and the surface treatment (especially the surface-crosslinking step) step are stopped in a heated state; and particularly preferably other steps (especially all steps) after the drying step in addition to the drying step and the surface treatment step (especially the surface-crosslinking step) are interrupted in a heated state. It is made possible to restart operation without any trouble and carry out stable operation by interrupting the steps in the heated state.

(Dry Air)

At the time of interruption of steps, from the viewpoint of retention of physical properties of the water-absorbing resin and suppression of the blocking phenomenon, it is preferable to inject dry air into the apparatuses of the interrupted steps. The dew point of the air may be not higher than 0° C.

(minus dew point), and is preferably −100 to −5° C., more preferably −95 to −30° C., still more preferably −90 to −35° C., and particularly preferably −85 to −40° C. A method for controlling the dew point of the air is not particularly limited and air may be properly dried by using appliances such as a membrane drier, a cooling adsorption type drier, and a diaphragm drier solely or in combination. In the case where a cooling adsorption type drier is used, it may be of heat regeneration manner, a non-heat regeneration manner, or a non-regeneration manner. The interruption of these steps means a state where an apparatus is unused, that is, a state where the water-absorbing resin is substantially absent and the water-absorbing resin is not charged to and not discharged out of an apparatus in each step.

[3] Physical Properties of Water-Absorbing Resin

The water-absorbing resin of the present invention contains a polyacrylic acid (salt)-type water-absorbing resin as a main component and obtained by the above-mentioned polymerization method, surface-crosslinking method, and the like, in the case where the water-absorbing resin is used for sanitary goods, particularly paper diapers. The obtained water-absorbing resin is preferable to control at least one of the following (3-1) to (3-6), further two or more including AAP, and particularly three or more. In the case the water-absorbing resin does not satisfy the following respective physical properties, there is a possibility that high concentration diapers containing not less than 40 mass % of the water-absorbing resin cannot sufficiently exhibit the performance.

(3-1) CRC (Absorption Capacity without Load)

The CRC (absorption capacity without load) of the water-absorbing resin to be obtained by the present invention is preferably 10 [g/g] or higher, more preferably 20 [g/g] or higher, still more preferably 25 [g/g] or higher, and particularly preferably 30 [g/g] or higher. The upper limit of the CRC is not particularly limited, is preferably 50 [g/g] or lower, more preferably 45 [g/g] or lower, still more preferably 40 [g/g] or lower. In the case the CRC is lower than 10 [g/g], the water absorption amount of the water-absorbing resin is small and the water-absorbing resin is possibly unsuitable for use for an absorbent body in sanitary goods such as paper diapers. In the case the CRC exceeds 50 [g/g], if the water-absorbing resin is used for such an absorbent body, it may possibly become impossible to obtain sanitary goods excellent in liquid intake speed and, therefore, it is not preferable. The CRC can be properly controlled by the above-mentioned internal crosslinking agent, surface-crosslinking agent, and the like.

(3-2) AAP (Absorption Capacity Under Load)

The AAP (absorption capacity under load) of the water-absorbing resin to be obtained by the present invention is preferably not lower than 20 [g/g], more preferably not lower than 22 [g/g], and still more preferably not lower than 24 [g/g] at a pressure of 4.83 kPa (0.7 psi) in order to prevent leakage in paper diapers. The upper limit of the AAP is not particularly limited; however, from the viewpoint of balance with other physical properties, it is preferably not higher than 40 [g/g]. In the case the AAP is lower than 20 [g/g], if the water-absorbing resin is used for an absorbent body, it may possibly become impossible to obtain sanitary goods with little liquid return (generally, also referred to as "Re-Wet") at the time a pressure is applied to the absorbent body and it is not preferable. The AAP can be properly controlled by the above-mentioned surface-crosslinking agent, the particle size, etc.

(3-3) SFC (Saline Flow Conductivity)

The SFC (saline flow conductivity) of the water-absorbing resin to be obtained by the present invention, which is a liquid permeability under pressure, is preferably $1[\times 10^{-7} \cdot cm^3 \cdot s \cdot g^{-1}]$ or higher, more preferably $10[\times 10^{-7} \cdot cm^3 \cdot s \cdot g^{-1}]$ or higher, still more preferably $50[\times 10^{-7} \cdot cm^3 \cdot s \cdot g^{-1}]$ or higher, particularly preferably $70[\times 10^{-7} \cdot cm^3 \cdot s \cdot g^{-1}]$ or higher, and most preferably $100[\cdot 10^{-7} \cdot cm^3 \cdot s \cdot g^{-1}]$ or higher in order to prevent leakage in paper diapers. The upper limit of the SFC is not particularly limited; however, from the viewpoint of balance with other physical properties, it is preferably not higher than $3000[\times 10^{-7} \cdot cm^3 \cdot s \cdot g^{-1}]$, more preferably not higher than $2000[\times 10^{-7} \cdot cm^3 \cdot s \cdot g^{-1}]$. In the case the SFC exceeds $3000[\times 10^{-7} \cdot cm^3 \cdot s \cdot g^{-1}]$, if the water-absorbing resin is used for such an absorber, liquid leakage may possibly occur in the absorber and, therefore it is not preferable. The SFC can be properly controlled by the above-mentioned drying method and the like.

(3-4) EXT (Amount of Water Soluble Components)

The EXT (amount of water soluble components) of the water-absorbing resin to be obtained by the present invention is preferably 35 mass % or lower, more preferably 25 mass % or lower, still more preferably 15 mass % or lower, and particularly preferably 10 mass % or lower. In the case the Ext exceeds 35 mass %, the water-absorbing resin to be obtained may possibly become weak in the gel strength and inferior in the liquid permeability. If such a water-absorbing resin is used for an absorber, it may possibly become impossible to obtain a water-absorbing resin with little liquid return (re-wet) at the time a pressure is applied to the absorber and it is not preferable. The Ext can be properly controlled by the above-mentioned internal crosslinking agent and the like.

(3-5) Residual Monomer

The residual Monomer amount of the water-absorbing resin to be obtained by the present invention, from the viewpoint of safety, is controlled to be preferably 0 to 400 ppm, more preferably 0 to 300 ppm, still more preferably 0 to 200 ppm. The residual monomer amount is controlled by the above-mentioned polymerization method and the like.

(3-6) Initial Color Hue

The water-absorbing resin to be obtained by the present invention is excellent in the initial color hue. The color hue (initial color hue) of a water-absorbing resin immediately after production obtained by the present invention shows the following numerical value. The initial color hue means the color hue immediately after production and in general, it is the color hue measured before shipment from a plant. It is also a value measured within 1 year from the production in the case of preservation in an atmosphere at not higher than 30° C. and a relative humidity of not higher than 50% RH. Concretely, in a Hunter Lab system, the L value (Lightness) is preferably not lower than 85, more preferably not lower than 87, and still more preferably not lower than 89. The b value is preferably −5 to 10, more preferably −5 to 9, still more preferably −4 to 8, and particularly preferably −1 to 7. The a value is preferably −2 to 2, more preferably −1 to 1, still more preferably −0.5 to 1, and particularly preferably 0 to 1. As another chromaticity, YI (Yellow Index) value is preferably not higher than 10, more preferably not higher than 8, and particularly preferably not higher than 6. As another chromaticity, the WB (White Balance) value is preferably not lower than 70, more preferably not lower than 75, and particularly preferably not lower than 77. The water-absorbing resin obtained by the present invention is excellent in coloration with time and shows sufficient whiteness in an accelerating test carried out in high temperature and high humidity.

[4] Use of Water-Absorbing Resin

Use of the water-absorbing resin obtained by the production process of the present invention is not particularly limited and the water-absorbing resin may be used for absorbing articles including sanitary goods such as paper diapers, sanitary napkins, and pads for incontinent, water retention agents for agriculture and horticulture, solidifying agents for waste liquids, industrial water shielding materials, and the like.

EXAMPLES

Hereinafter, the present invention will be described in detail with reference to examples and comparative examples; however, the present invention should not be construed in a limited way based on the description of the examples. For convenience, "litter" is expressed as "L" and "mass %" as "wt %" in some cases. The various physical properties described in CLAIMS and Examples of a water-absorbing resin obtained by the present invention were measured according to EDANA method and the following measurement examples under the condition of room temperature (20 to 25° C.) and a humidity of 50% RH unless otherwise specified.

1. Initial Color Hue and Coloration with Time The initial color hue and coloration with time of a water-absorbing resin of the present invention were measured according to measurement methods described in WO No. 2009/005114 pamphlet.

2. Resin Solid Content (Solid Content)

A water-absorbing resin in an amount of 1.00 g was weighed in an aluminum cup with a bottom surface diameter of about 50 mm and the total weight W1 [g] of the sample (the water-absorbing resin and the aluminum cup) was accurately weighed.

Next, the sample was stood still in an oven at an atmosphere temperature of 180° C. and the water-absorbing resin was dried. After 3 hours, the sample in the aluminum cap was taken out of the oven and cooled to room temperature in a desiccator. Thereafter, the total weight W2 [g] of the sample (the water-absorbing resin and the aluminum cup) after drying was measured and the solid content (unit; [mass %]) was calculated according to the following expression.

Solid content[wt %]=100−{(W1−W2)/(weight of water-absorbing resin [g])×100}   [Mathematic 1]

In the case of measuring the resin solid content of a particulated water-containing gel-like crosslinked polymer (particulated hydrogel), the sampling amount of the particulated hydrogel was changed to be 2 to 4 g and the drying time was changed to be 24 hours.

3. SFC (Saline Flow Conductivity)

The SFC (saline flow conductivity) of the water-absorbing resin to be obtained by the present invention was measured according to the description in the specification of U.S. Pat. No. 5,669,894.

4. Other Physical Properties

The physical properties of a water-absorbing resin to be obtained by the present invention, that is, CRC (absorption capacity without load), particle size distribution, pH soluble matter, remaining acrylic acid amount, and the like were measured according to ERT of EDANA or the description in the specification of US Patent Application Publication No. 2006/204755.

Example 1

A water-absorbing resin was produced by using a continuous production apparatus involving a continuous polymerization step, a drying step by a band drier, a pulverizing step, a classification step, a surface treatment step (a wetting and a mixing step, a heating step, and a cooling step), a particle regulation step, and a conveying step for joining the respective steps. An intermediate hopper was installed between the drying step and the pulverizing step.

0.04 g of sodium persulfate (relative to 1 mol of monomer) and 100 ppm of diethylenetriamine pentaacetic acid pentasodium salt were continuously mixed by line mixing with an aqueous solution of acrylic acid sodium salt partially neutralized in an amount of 70 mol % (monomer concentration: 53 mass %) containing 0.03 mol % (based on monomer) of polyethylene glycol diacrylate (average molecular weight: 478) as an internal crosslinking agent and the mixture was supplied to a belt polymerization apparatus and subjected to aqueous solution polymerization. The hydrogel obtained in this manner was finely crushed by a vertical crusher (manufactured by Orient Co., Ltd., screen of 12 mm) to obtain a particulated water-containing gel-like polymer (1) containing 70 mass % of solid content and having fluidity.

The particulated water-containing gel-like polymer (1) was continuously layered by using a traverse feeder for a continuous air ventilating belt type dryer on a punching metal of an air ventilating belt which was continuously operated by controlling the sequence of the traverse feeder and continuously dried on the air ventilating belt for 35 minutes. The discharge amount (treatment amount) of the dried material was 1.7 [t/hr]. The dying apparatus and drying condition were as shown in the following (a) to (c).

(a) Belt Type Dryer

A dryer used was a continuous air ventilating dryer having 6 drying chambers in total which can independently adjust the hot air temperature and which have the same size and in which an air ventilating belt passes. The hydrogel passed in about 5.8 minutes (=35 min/6 chambers on the belt) in the respective 6 drying chambers.

(b) Hot Air Temperature and Linear Velocity

The hot air temperature of the drying chambers was heated to be 180° C. by steam and the linear velocity of the hot air was set to be 1.6 m/s. The blow direction of the first chamber was upward from the bottom surface and the blow direction of the second to the sixth chambers was set downward to the bottom surface from an upper part of the dryer.

(c) Air Ventilating Belt

The ventilating belt used was a stainless steel belt (band) made of SUS 304 and having long round holes with a width of 1.2 mm and a length of 15 mm in a zigzag arrangement and a hole ratio of 27%.

The particulated water-containing gel-like polymer was agglomerated like blocks at the time of drying. After loosened into several millimeters, the entire amount of the loosened dried product was continuously supplied to a roll mill (roll gaps: 1.0 mm/0.55 mm/0.42 mm from the upper side) and pulverized and classified with a sieving apparatus having a metal sieving net with meshes of 850 μm to obtain a water-absorbing resin powder (A).

The water-absorbing resin powder (A) was continuously supplied to a high speed continuous mixing apparatus (Turbulizer; 1000 rpm) by pneumatic transportation (temperature 35° C. and dew point −15° C.) from the classifying apparatus at 1.5 t/hr and at the same time a surface treatment agent solution (1) was mixed by spraying (wetting and mixing step). The surface treatment agent solution (1) was a mixed solution containing 1,4-butanediol, propylene glycol, and pure water. The surface treatment agent solution (1) was mixed with the water-absorbing resin powder (A) at a ratio of 0.3 parts by mass of 1,4-butanediol, 0.5 parts by mass of propylene glycol, and 2.7 parts by mass of pure water relative to 100 parts by mass of the water-absorbing resin powder (A) to give a mixture (A), a wet powder.

The obtained mixture (1) was then surface-treated by a transverse type continuous stirring apparatus (1) having a downward inclined angle of 1°, an aspect ratio of 2.2, a paddle rotation speed of 13 rpm, scraping blades, two rotary shafts having a surface roughness (Rz) of the inner surface of 500 nm (heating treatment step). At that time, the inside of the apparatus (1) was suctioned by a suctioning gas discharge apparatus having a bag filter, and the inside pressure of the apparatus was reduced to 1 kPa. A rotary valve (periodically shielding apparatus) was installed in the inlet and outlet of the apparatus (1). According to a previous test, the position of a discharge bank which gave an average retention time of about 45 minutes and an average filling ratio of 75% was obtained, and the discharge bank was set at the position as obtained. A heating source used for the surface treatment was pressurized steam at 2.5 MPa, and the temperature of the mixture (1) in the apparatus was measured by a thermometer installed near the discharge part of the transverse type continuous stirring apparatus (1), and the steam flow rate was controlled to carry out the heating in such a manner that the temperature was adjusted to 198° C. The total surface area of the stirring disks and the stirring shafts was 24.4 m² and the mass surface area ratio calculated from the total surface area (heat transfer surface area) and the treatment amount was 61.5 [kg/m²/hr]. The stirring power at the time of the surface treatment was 27.8 kW, the stirring power in idling was 13.5 kW, the average retention time was 45 minutes, and the stirring power index was 9.5[W·hr/kg]. Using same transverse type continuous stirring apparatus so that the water absorbent resin was forcibly cooled to 60° C. (cooling step).

The water-absorbing resin (A) which was a adjusted substance all under 850 μm as a product was obtained by carrying out classification by a sieving apparatus to separate the substance under 850 μm, and mixing the substance on 850 μm (substance that did not pass through 850 μm) after pulverized again with the substance under 850 μm.

In the above-mentioned operation, the classification step was interrupted for 1 hour in order to change a metal net (from 850 μm to 710 μm) of the sieving apparatus for the classification step. During the interruption period in the classification step, the polymerization step and the drying step, which are joined presteps, were run as they were and after the agglomerated dried material from the band drier was roughly crushed (loosened) to several millimeters, the resulting material was temporarily stored in the intermediate hopper (temperature 60° C.) before the pulverizer.

The size of the hopper was 15 m³ and the filling ratio at the time of normal continuous operation was 0%. The filling ratio of the hopper became 20% over 1 hour when the classification step was interrupted. After the metal net of the sieving apparatus in the classification step was changed, supply of the dried material (several millimeters corresponding to 1 hour storage and its dried material) was restarted to the crushing step from the hopper at a filling ratio of 20%. Stable and continuous production could be carried out without interrupting the polymerization step and the drying step in the above-mentioned manner.

Comparative Example 1

No intermediate hopper was used or installed before the pulverizer in Example 1. That is, during the interruption period of 1 hour in the classification step, the polymerization step and the drying step, which are joined presteps, were completely stopped and the respective steps such as the pulverizing step and the classification step were also simultaneously and completely stopped. At the time of restarting of operation, excess load to a drying belt (increase of power consumption) was found and at the time of rotation of the band drier made of stainless steel, abnormal noise was generated.

Continuous production (preferably not shorter than 10 days) of a water-absorbing resin in a huge scale (preferably not less than 1 [t/hr]) is made possible by using an intermediate hopper. The conventional production processes described in Patent Documents 1 to 13 do not at all imply the stopping method of the present invention and its effect.

INDUSTRIAL APPLICABILITY

A water-absorbing resin free from coloration and a foreign matter can be produced economically and stably by continuous production in a huge scale (e.g., 1 [t/hr] or more) and the water-absorbing resin of the present invention can be used for various kinds of sanitary materials such as paper diapers and sanitary napkins and also for various applications.

The invention claimed is:

1. A process for producing a water-absorbing resin comprising a plurality of joined continuous steps; a polymerization step of polymerizing an aqueous unsaturated monomer solution, a drying step of drying a particulated water-containing gel-like crosslinked polymer obtained in a finely crushing step during the polymerization or after the polymerization, a pulverizing step after the drying, a classification step after the drying, and a surface treatment step for the water-absorbing resin powder after the classification step, wherein with some of the above steps kept running continuously, the other steps are interrupted, and subsequently the interrupted steps are restarted, the interruption of the steps are at least one selected from the group of an interruption at the time of periodic maintenance and a temporal trouble, at least one of the interrupted steps is selected from the group consisting of the polymerization step, the drying step, the pulverizing step, the classification step, and the surface treatment step, a particulated water-containing gel-like crosslinked polymer, a dried material thereof, or a water-absorbing resin powder is substantially absent from an apparatus for the at least one interrupted step, the apparatus is kept in a heated state during the interruption of the step, or dry air having a dew point of not higher than 0° C. is injected into the apparatus for the interrupted step, wherein substantially absent means the particulated water-containing gel-like crosslinked polymer, dried material thereof, or water-absorbing resin powder is taken out of the apparatus for the interrupted step in an amount of not less than 95 mass % based on the entire retention capability of the apparatus;

the continuously running steps before the interrupted steps are kept running by storing the water-absorbing resin to be charged to the interrupted steps by installing a storage step for temporarily storing the water-absorbing resin, the storage step comprising an un-filled hopper or a hopper with a low filling ratio for temporarily storing the water-absorbing resin, the unfilled hopper or the hopper with the low filling ratio is installed between the drying step and either the pulverizing step or the classification step after the drying to temporarily store the water-absorbing resin after the drying at the time of interrupting the pulverizing step or the steps after the classification step, the filling ratio of the un-filled hopper or the hopper with a low filling ratio is 0 to 50%, the interrupted steps are restarted after countermeasures for the periodic maintenance and the temporal trouble are made.

2. The production process according to claim 1, wherein the step to be interrupted is the classification step or the pulverizing step.

3. The production process according to claim 1, wherein the water-absorbing resin is produced at not less than 1 ton/hr.

4. The production process according to claim 1, wherein the respective steps after the drying step are interrupted while apparatuses used in the respective interrupted steps being kept in a heated state and subsequently, the respective interrupted steps are restarted.

5. The production process according to claim 1, wherein a surface-crosslinking agent to be used in the surface treatment step is a dehydration reactive surface-crosslinking agent.

6. The process of claim 1, wherein said dry air is injected into the apparatus for the at least one interrupted step.

7. The process of claim 1, wherein the apparatus for the at least one interrupted step is maintained in a heated state during the interruption of the respective step.

8. The process of claim 1, wherein the apparatus for the at least one interrupted step is kept in a heated state without heating the classification apparatus for the classification step.

9. The production process according to claim 1, wherein the apparatus for at least one of the interrupted steps is stopped while kept in a heated state during the interruption of the step.

10. The production process according to claim 1, wherein the apparatus for the polymerization is a polymerization apparatus, the apparatus for the drying step is a dryer, the apparatus for the pulverizing step is a pulverizer, the apparatus for the classification step is a classification apparatus, and the apparatus for the surface treatment step is a heating treatment apparatus and/or a cooling apparatus.

11. A process for producing a water-absorbing resin comprising a plurality of joined continuous steps; a polymerization step of polymerizing an aqueous unsaturated monomer solution, a drying step of drying a particulated water-containing gel-like crosslinked polymer obtained in a finely crushing step during the polymerization or after the polymerization, a pulverizing step after the drying, a classification step after the drying, and a surface treatment step for the water-absorbing resin powder after the classification step, wherein with some of the above steps kept running continuously, the other steps are interrupted, and subsequently the interrupted steps are restarted, the interruption of the steps are at least one selected from the group of an interruption at the time of periodic maintenance and a temporal trouble, at least one of the interrupted steps is selected from the group consisting of the polymerization step, the drying step, the pulverizing step, the classification step, and the surface treatment step, a articulated water-containing gel-like crosslinked polymer, a dried material thereof, or a water absorbing resin powder is substantially absent from an apparatus for the at least one interrupted step, the apparatus is kept in a heated state during the interruption of the step, or dry air having a dew point of not higher than 0° C. is injected into the apparatus for the interrupted step, wherein substantially absent means the particulated water-containing gel-like crosslinked polymer, dried material thereof, or water-absorbing resin powder is taken out of the apparatus for the interrupted step in an amount not less than 95 mass % based on the entire retention capability of the apparatus;

the continuously running steps before the interrupted steps are kept running by storing the water-absorbing resin to be charged to the interrupted steps by a storage step for temporarily storing the water-absorbing resin, the storage step comprising an un-filled hopper or a hopper with a low filling ratio for temporarily storing the water-absorbing resin, the unfilled hopper or the hoper with the low filling ratio is installed between the classification step and the surface treatment step to temporarily store the water-absorbing resin after the classification at the time of interrupting the steps after the surface treatment step, the filling ratio of the un-filled hopper or the hopper with the low filling ratio is 0 to 50%, the interrupted steps are restarted after countermeasures for the periodic maintenance and the temporal trouble are made.

12. The production process according to claim 11, wherein the capacity of the hopper is not less than 20% of the production quantity of the water-absorbing resin per hour.

13. The production process according to claim 12, wherein the hopper is heated to not lower than 40° C.

14. The process of claim 11, wherein said dry air in injected into the apparatus for the at least one interrupted step.

15. The process of claim 11, wherein the apparatus for the at least one interrupted step is maintained in a heated state during the interruption of the respective step.

16. The process of claim 11, wherein the apparatus for the at least one interrupted step is kept in a heated state without heating the classification apparatus for the classification step.

* * * * *